(12) United States Patent
Debinski et al.

(10) Patent No.: US 9,005,600 B2
(45) Date of Patent: *Apr. 14, 2015

(54) COMPOUNDS USEFUL FOR MULTI-LEVEL SPECIFIC TARGETING OF CANCER CELLS

(71) Applicant: Wake Forest University Health Sciences, Winston-Salem, NC (US)

(72) Inventors: Waldemar Debinski, Winston-Salem, NC (US); Hetal Pandya, Winston-Salem, NC (US); Denise Gibo, Winston-Salem, NC (US)

(73) Assignee: Wake Forest University Health Sciences, Winston-Salem, NC (US)

(*) Notice: Subject to any disclaimer, the term of this patent is extended or adjusted under 35 U.S.C. 154(b) by 65 days.

This patent is subject to a terminal disclaimer.

(21) Appl. No.: 13/718,166

(22) Filed: Dec. 18, 2012

(65) Prior Publication Data

US 2013/0164257 A1 Jun. 27, 2013

Related U.S. Application Data

(63) Continuation of application No. 13/086,698, filed on Apr. 14, 2011, now Pat. No. 8,362,207.

(60) Provisional application No. 61/324,952, filed on Apr. 16, 2010.

(51) Int. Cl.

| | |
|---|---|
| *C07K 14/54* | (2006.01) |
| *A61K 38/20* | (2006.01) |
| *C07K 14/21* | (2006.01) |
| *C07K 19/00* | (2006.01) |
| *C07K 14/34* | (2006.01) |
| *G01N 33/50* | (2006.01) |
| *G01N 33/532* | (2006.01) |
| *G01N 33/68* | (2006.01) |
| *A61K 38/00* | (2006.01) |

(52) U.S. Cl.
CPC ............ *C07K 14/21* (2013.01); *C07K 19/00* (2013.01); *C07K 14/34* (2013.01); *G01N 33/5008* (2013.01); *G01N 33/5091* (2013.01); *G01N 33/532* (2013.01); *G01N 33/6869* (2013.01); *A61K 38/00* (2013.01); *C07K 2319/01* (2013.01)

(58) Field of Classification Search
CPC ..... A61K 38/00; C07K 14/21; C07K 2319/01
USPC .................... 530/351, 402; 424/85.2
See application file for complete search history.

(56) References Cited

U.S. PATENT DOCUMENTS

| | | |
|---|---|---|
| 5,328,984 A | 7/1994 | Pastan et al. |
| 5,614,191 A | 3/1997 | Puri et al. |
| 5,919,456 A | 7/1999 | Puri et al. |
| 6,022,735 A | 2/2000 | Curiel et al. |
| 6,235,526 B1 | 5/2001 | Sedlacek et al. |
| 6,274,322 B1 | 8/2001 | Curiel et al. |
| 6,296,843 B1 | 10/2001 | Debinski |
| 6,428,788 B1 | 8/2002 | Debinski et al. |
| 6,518,061 B1 | 2/2003 | Puri et al. |
| 6,576,232 B1 | 6/2003 | Debinski et al. |
| 6,630,576 B2 | 10/2003 | Debinski |
| 6,884,603 B2 | 4/2005 | Debinski et al. |
| 6,949,245 B1 | 9/2005 | Sliwkowski |
| 7,332,586 B2 | 2/2008 | Franzen et al. |
| 7,498,177 B2 | 3/2009 | De La Fuente et al. |
| 7,517,964 B2 | 4/2009 | Govindan et al. |
| 7,531,624 B2 | 5/2009 | Banes et al. |
| 7,550,650 B2 | 6/2009 | Rapp et al. |
| 7,585,636 B2 | 9/2009 | Waldo et al. |
| 8,362,207 B2 * | 1/2013 | Debinski et al. .............. 530/351 |
| 2001/0046498 A1 | 11/2001 | Ruoslahti et al. |
| 2006/0121539 A1 | 6/2006 | Debinski et al. |

OTHER PUBLICATIONS

Pandya H et al. Molecular targeting of intracellular compartments specifically in cancer cells. Genes & Cancer. 2010; 1(5); 421-433.

* cited by examiner

*Primary Examiner* — Prema Mertz
(74) *Attorney, Agent, or Firm* — Myers Bigel Sibley & Sajovec, P.A.

(57) ABSTRACT

A compound comprising, in combination: a cell surface binding ligand or internalizing factor, such as an IL-13Rα2 binding ligand; at least one effector molecule (e.g., one, two, three or more effector molecules); optionally but preferably, a cytosol localization element covalently coupled between said binding ligand and said at least one effector molecule; and a subcellular compartment localization signal element covalently coupled between said binding ligand and said at least one effector molecule (and preferably with said cytosol localization element between said binding ligand and said subcellular compartment localization signal element). Methods of using such compounds and formulations containing the same are also described.

20 Claims, No Drawings

COMPOUNDS USEFUL FOR MULTI-LEVEL SPECIFIC TARGETING OF CANCER CELLS

RELATED APPLICATIONS

This application is a continuation of and claims priority to U.S. patent application Ser. No. 13/086,698, filed Apr. 14, 2011, now allowed, which claims the benefit of U.S. Provisional Patent Application Ser. No. 61/324,952, filed Apr. 16, 2010, the disclosure of each of which is incorporated by reference herein in its entirety.

GOVERNMENT FUNDING

This invention was made with United States government support under grant number RO1 CA 74145 from the National Institutes of Health. The United States government has certain rights to this invention.

FIELD OF THE INVENTION

The present invention concerns methods and constructs for delivering compounds of interest to cells, particularly cells that express IL-13 receptors.

BACKGROUND OF THE INVENTION

Molecular targeting of cancer cells is achieved (a) specifically through the use of ligands/antibodies against tumor-associated or tumor-specific receptors, and (b) non-specifically using plasma membrane permeable agents targeting activated/over-expressed intracellular elements, such as the oncogenes. In the field of non-viral gene therapy of cancer that employs recombinant proteins, the inventors have pioneered the use of proteinaceous vectors for the targeted intracellular transport of proteins/non-proteinaceous compounds (1-3). Some bacterial toxins, such as *Pseudomonas* exotoxin A (PE) or Diphtheria toxin (DT), possess an ability to exit the endocytic compartment after being internalized in the process of receptor-mediated internalization and being proteolytically activated by a calcium-dependent serine endoprotease, furin (4-7). This "get cleaved and exit endocytic compartment" ability is possible due to the presence of a specialized domain of PE, domain II (abbreviated here D2) (8; 9).

Previously, the inventors have exploited PE translocation ability to traffic other, non-PE, or repeated PE peptide sequences into the cell cytosol (1). This was achieved by incorporating non-PE peptides or an additional catalytic domain III of PE within dispensable domain Ib. This domain is downstream of both furin cleavage site and a cleavage-created N-terminal sequence important for initiation/conduct of the C-terminal portion of the toxin (portion of domain 2 and domain 3) endocytic vesicles exit. The inventors demonstrated for the first time that in this manner, PE can serve as a vector for intra-cytosolic delivery of various proteins (1).

Most anti-cancer therapeutics have defined targets such as oncogenes, enzymes or DNA, all of which are localized to distinct intra-cellular compartments like nucleus, mitochondria or cytosol. GBM is a high-grade astrocytoma representing the most common form of primary brain tumors. The successful treatment of patients with GBM is still a major challenge and the median survival rate is 14.5 months after diagnosis (12). Several factors specific to GBM have been uncovered in recent years (13-16). For example, a tri-molecular signature of GBM has been documented that includes IL-13Rα2, EphA2 receptor and a fos-related antigen 1 (Fra-1) (17). All three factors belonging to the signature are suitable for therapeutic targeting of GBM (18). IL-13Rα2 is expressed in >75% of GBM tumor specimens (19; 20) and is characterized as a cancer/testes like antigen (21). IL-13Rα2 is believed to act as a decoy receptor (22). However, it has been shown that IL-13 ligand binds to IL13Rα2 receptor and is internalized through receptor mediated endocytosis (23; 24). Thus, drugs attached to the IL-13 ligand can be internalized and delivered specifically inside the glioma cells.

SUMMARY OF THE INVENTION

A first aspect of the invention is a compound comprising, in combination: a cell surface binding ligand or internalizing factor, such as an IL-13Rα2 binding ligand; at least one effector molecule (e.g., one, two, three or more effector molecules); optionally but preferably, a cytosol localization element covalently coupled between said binding ligand and said at least one effector molecule; and a subcellular compartment localization signal element covalently coupled between said binding ligand and said at least one effector molecule (and preferably with said cytosol localization element between said binding ligand and said subcellular compartment localization signal element).

In some embodiments, the compound has the formula, from N terminus to C terminus, selected from the group consisting of: A-B-C-D-E; E-D-C-B-A; A-B-D-C-E; and E-C-D-B-A, wherein: A is an internalizing factor or binding element such as an IL-13Rα2 binding ligand; B is the cytosol localization element; C is the subcellular compartment localization signal element; D is present or absent and when present a first effector molecule; and E is present or absent and when present is a second effector molecule. As will be appreciated, additional effector molecules (e.g., three or more effector molecules) can be included if so desired.

In some embodiments, the compound is a fusion protein or covalent conjugate.

In some embodiments, each of A, B, and C, and optionally D and E, is a peptide.

In some embodiments, the cytosol localization element is a *Pseudomonas* or diphtheria toxin translocation domain, such as a *Pseudomonas* exotoxin A D2 segment.

In some embodiments, the subcellular compartment localization signal element is a nuclear localization element or a lysosomal localization element, such as an SV40 T antigen nuclear localization signal.

In some embodiments, wherein said IL-13Rα2 binding ligand is IL-13, a mutant of IL-13, or an IL-13Rα2 binding fragment thereof.

A further aspect of the invention is a nucleic acid that encodes a compound as described above, along with host cells that contain and express the same.

A further aspect of the invention is a method of treating and/or detecting cancer in a subject in need thereof, comprising administering said subject a compound as described herein in a treatment and/or detection effective amount. The cancer may be, for example, breast cancer, bladder cancer, pancreatic cancer, colorectal cancer, head and neck cancer, thyroid cancer, prostate cancer, and gliomas such as glioblastoma multiforme.

A further aspect of the invention is a method of detecting IL-13Rα2 expressing cells, comprising administering a compound as described herein to a cell or group of cells in vitro or in vivo, and detecting a detectable group coupled to said compound.

A further aspect of the invention is a method of delivering at least one effector molecule (e.g., a detectable group or a therapeutic group) to a subcellular compartment of a cell of interest, comprising: contacting a compound as described herein including at least one effector molecule (e.g., as either D or E) to a cell of interest (e.g., a eukaryotic cell, in vitro or in vivo) under conditions in which said compound is internalized therein and said effector molecule is delivered to said subcellular compartment (e.g., the nucleus). In some embodiments, the compound further comprises an additional effector molecule (e.g., as either D or E). In some embodiments, the additional effector molecule is delivered to the cytosol of the cell of interest (e.g., wherein said compound is of the formula A-B-D-C-E or E-C-D-B-A). The method is useful for research purposes (e.g., labeling subcellular compartments), and for the methods of diagnosis and treatment described herein.

A further aspect of the invention is the use of a compound as described herein for carrying out a method as described herein, and/or for the preparation of a medicament as described herein.

DETAILED DESCRIPTION OF THE PREFERRED EMBODIMENTS

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

The disclosures of all United States patents cited herein are to be incorporated herein by reference in their entirety.

A. Definitions

"Capping group" as used herein includes, but is not limited to, acetyl, benzoyl, formyl, trifluoroacetyl, benzyloxycarbonyl, tert-butyloxycarbonyl, biphenylylisopropyloxycarbonyl, triphenylmethyl, o-nitrobenzenesulfenyl, and diphenylphosphinyl. The capping groups may consist of such groups as $R^{10}CO-$, $R^{10}-O-CO-$, $R^{10}-PO-$, $R^{10}-SO_2-$ and arylalkyl-; where $R^{10}$ is selected from the group consisting of H, alkyl, alkenyl, alkynyl, aryl, and arylalkyl.

"Alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like.

"Alkenyl," as used herein, refers to a straight or branched chain hydrocarbon containing from 2 to 10 carbons and containing at least one carbon-carbon double bond formed by the removal of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. "Lower alkenyl" as used herein, is a subset of alkenyl and refers to a straight or branched chain hydrocarbon group containing from 2 to 4 carbon atoms.

"Alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, 1-butynyl and the like. "Lower alkynyl" as used herein, is a subset of alkyl and refers to a straight or branched chain hydrocarbon group containing from 2 to 4 carbon atoms.

The alkyl, alkenyl, and alkynyl groups of the invention can be substituted or unsubstituted and are either unless otherwise specified. When substituted the alkyl, alkenyl or alkynyl groups of the invention can be substituted with 1, 2, 3, 4, or 5 or more substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, "Aryl" as used herein, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like.

The aryl groups of this invention can be substituted with 1, 2, 3, 4, or 5 or more substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, "Arylalkyl," as used herein, refers to an aryl group, as defined herein, appended to the parent molecular moiety through an alkenyl group, as defined herein. Representative examples of arylalkenyl include, but are not limited to, 2-phenylethenyl, 3-phenylpropen-2-yl, 2-naphth-2-ylethenyl, and the like, which may be substituted or unsubstituted as noted above.

"IL13" or "IL-13" as used herein refers to interleukin-13, which is a pleiotropic cytokine. IL-13 has approximately 30% sequence identity with IL4 and exhibits IL4-like activities on monocytes/macrophages and human B cells (Minty et al. (1993) Nature 362:248; McKenzie et al. (1987) Proc. Natl. Acad. Sci. USA 90:3735). In particular, IL-13 appears to be a potent regulator of inflammatory and immune responses. IL-13 can up-regulate the monocyte/macrophage expression of CD23 and MHC class I and class II antigens, down-regulate the expression of Fc.gamma, and inhibit antibody-dependent cytotoxicity. IL-13 can also inhibit nitric oxide production as well as the expression of pro-inflammatory cytokines (e.g., IL-1, IL-6, IL-8, IL-10 and IL-12) and chemokines (MIP-1, MCP), but enhance the production of IL-1.

"Recombinant" nucleic acid as used herein refers to a nucleic acid produced by combining two or more nucleic acid sequences from different sources, e.g., by use of molecular biology techniques, to form a new nucleic acid, e.g., a "heterologous" nucleic acid. The recombinant nucleic acid may be provided in the form of a "vector" or "delivery vector" in order to transform or transfect cells to contain the new nucleic acid. As used herein, a "vector" or "delivery vector" can be a viral or non-viral vector that is used to deliver a nucleic acid to a cell, tissue or subject.

A "recombinant" protein is a protein produced by a recombinant nucleic acid. The nucleic acid may or may not be inserted into the genome of a host cell. The nucleic acid may exist, e.g., in plasmid form in a host cell. Alternatively, the recombinant protein may be produced by in vitro translation of the recombinant nucleic acid.

An "isolated" protein or polypeptide means a protein or polypeptide that is separated or substantially free from at least some of the other components of the naturally occurring organism or virus, for example, the cell or viral structural components or other proteins or nucleic acids commonly found associated with the protein. As used herein, the "isolated" protein or polypeptide is at least about 25%, 30%, 40%, 50%, 60%, 70%, 75%, 80%, 85%, 90%, 95%, 97%, 98%, 99% or more pure (w/w).

"Subjects" as used herein are generally human subjects and includes, but is not limited to, cancer patients. The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric. Subjects may also include animal subjects, particularly mammalian subjects such as canines, felines, bovines, caprines, equines, ovines, porcines, rodents (e.g. rats and mice), lagomorphs, primates (including non-human primates), etc., screened for veterinary medicine or pharmaceutical drug development purposes.

"Cancer" or "cancers" that can be detected and/or treated by the compounds, compositions and methods described herein include, but are not limited to, breast cancer, bladder cancer, pancreatic cancer, colorectal cancer, head and neck cancer, thyroid cancer, prostate cancer, and brain cancer such as gliomas (e.g., GBM), etc.

"Effector molecule" as used herein includes therapeutic agents, detectable groups, targeting ligands, and delivery vehicles (e.g., antibodies, lipids, liposomes). See, e.g., U.S. Pat. No. 6,630,576.

"Therapeutic agent" as used herein may be any therapeutic agent including, but not limited to, genetic materials or agents, radionuclides, chemotherapeutic agents, and cytotoxic agents (See, e.g., U.S. Pat. No. 6,949,245 to Sliwkowski), and amphipathic antimicrobial peptides. Other exemplary therapeutic agents include, but are not limited to, radiopharmaceuticals, including, but not limited to auger electrons, chemotherapeutics, and photosensitizers.

"Radionuclide" as described herein includes, but is not limited to, $^{227}$Ac, $^{211}$At, $^{131}$Ba, $^{77}$Br, $^{109}$Cd, $^{51}$Cr, $^{67}$Cu, $^{165}$Dy, $^{155}$Eu, $^{153}$Gd, $^{198}$Au, $^{166}$Ho, $^{113m}$In, $^{115m}$In, $^{123}$I, $^{125}$I, $^{131}$I, $^{189}$Ir, $^{191}$Ir, $^{192}$Ir, $^{194}$Ir, $^{52}$Fe, $^{55}$Fe, $^{59}$Fe, $^{177}$Lu, $^{109}$Pd, $^{32}$P, $^{226}$Ra, $^{186}$Re, $^{188}$Re, $^{153}$Sm, $^{46}$Sc, $^{47}$Sc, $^{72}$Se, $^{75}$Se, $^{105}$Ag, $^{89}$Sr, $^{35}$S, $^{177}$Ta, $^{117m}$Sn, $^{121}$Sn, $^{166}$Yb, $^{169}$Yb, $^{90}$Y, $^{212}$Bi, $^{119}$Sb, $^{197}$Hg, $^{97}$Ru, $^{100}$Pd, $^{101m}$Rh, and $^{212}$Pb.

"Chemotherapeutic agent" as used herein includes, but is not limited to, methotrexate, daunomycin, mitomycin C, cisplatin, vincristine, epirubicin, fluorouracil, verapamil, cyclophosphamide, cytosine arabinoside, aminopterin, bleomycin, mitomycin C, democolcine, etoposide, mithramycin, chlorambucil, melphalan, daunorubicin, doxorubicin, tamosifen, paclitaxel, vincristin, vinblastine, camptothecin, actinomycin D, and cytarabine. Other examples are found in U.S. Patent Application Publication 2006/0121539 (Debinski et al.), which is incorporated by reference herein in its entirety.

"Cytotoxic agent" or "toxic agent" as used herein includes, but is not limited to, maytansinoids and maytansinoid analogs, taxoids, CC-1065 and CC-1065 analogs, dolastatin and dolastatin analogs, ricin (or more particularly the ricin A chain), aclacinomycin, Diphtheria toxin, Monensin, Verrucarin A, Abrin, Tricothecenes, and Pseudomonas exotoxin A, taxol, cytochalasin B, gramicidin D, ethidium bromide, emetine, mitomycin, etoposide, tenoposide, anti-mitotic agents, such as the vinca alkaloids (e.g., vincristine and vinblastine), colchicin, anthracyclines, such as doxorubicin and daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof, antimetabolites (e.g., methotrexate, 6-mercaptopurine, 6-thioguanine, cytarabine, and 5-fluorouracil decarbazine), alkylating agents (e.g., mechlorethamine, thioepa chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP)), and antibiotics, including, but not limited to, dactinomycin (formerly actinomycin), bleomycin, mithramycin, calicheamicin, and anthramycin (AMC)).

In some embodiments, cytotoxic agents include toxins such as Pseudomonas exotoxin, ricin, abrin, ribonuclease (RNase), DNase I, Staphylococcal enterotoxin-A, pokeweed antiviral protein, gelonin, diphtheria toxin, etc. See, e.g., U.S. Pat. No. 7,517,964. In some embodiments, Pseudomonas exotoxin or a Diphtheria toxin are preferred. See U.S. Pat. No. 5,328,984 to Pastan et al. and U.S. Pat. No. 6,296,843 to Debinski, which are each incorporated by reference herein in its entirety. Pseudomonas exotoxins can include, but are not limited to, Pseudomonas exotoxin A (PE). The Pseudomonas exotoxin can be modified such that it substantially lacks domain Ia, and in some embodiments Pseudomonas exotoxins include PE38QQR and PE4E. Diphtheria toxins can include DT390, a diphtheria toxin in which the native binding domain is eliminated. It will be appreciated that in various embodiments, the therapeutic agents can be attached to, e.g., the amino terminus or the carboxyl terminus.

"Amphipathic antimicrobial peptide" as used herein includes amphipathic peptides that induce apoptosis of cancer cells, presumably through their ability to depoarize mitochondrial membranes. K. Rege et al., Cancer Res. 67, 6368 (Jul. 1, 2007). Such peptides are, in general, from 10, 12 or 13 to 20, 30 or 40 amino acids in length, or more, and typically have an amphipathic alpha-helical structure. Examples include, but are not limited to, (KLAKLAK)$_2$ (SEQ ID NO: 60); (KLAKKLA)$_2$ (SEQ ID NO: 61) (KAAKKAA)$_2$ (SEQ ID NO: 62) and (KLGKKLG)$_2$ (SEQ ID NO: 63) See, e.g., Ruoslahti et al., US Patent Application 20010046498 (Nov. 29, 2001).

"Detectable group" or "label" as used herein includes, but is not limited to, radiolabels (e.g., $^{35}$S, $^{125}$I, $^{32}$P, $^3$H, $^{14}$C, $^{131}$I), enzyme labels (e.g., horseradish peroxidase, alkaline phosphatase), gold beads, chemiluminescence labels, ligands (e.g., biotin, digoxin) and/or fluorescence labels (e.g., rhodamine, phycoerythrin, fluorescein, fluorescent proteins), a fluorescent protein including, but not limited to, a green fluorescent protein or one of its many modified forms, a nucleic acid segment in accordance with known techniques, and energy absorbing and energy emitting agents. Thus "label" or "detectable group" as used herein may be any suitable label or detectable group detectable by spectroscopic, photochemical, biochemical, immunochemical, electrical, optical or chemical means including but not limited to biotin, fluorophores, antigens, porphyrins, and radioactive isotopes. Labels useful in the present invention include biotin for staining with labeled avidin or streptavidin conjugate, magnetic beads (e.g., Dynabeads™), fluorescent dyes (e.g., fluorescein, fluorescein-isothiocyanate [FITC], Texas red, rhodamine, green fluorescent protein, enhanced green fluorescent protein, lissamine, phycoerythrin, Cy2, Cy3, Cy3.5, Cy5, Cy5.5, Cy7, FluorX [Amersham], SyBR Green I & II [Molecular Probes], and the like), radiolabels (e.g., $^3$H, $^{35}$S, $^{14}$C, or $^{32}$P), enzymes (e.g., hydrolases, particularly phosphatases such as alkaline phosphatase, esterases and glycosidases, or oxidoreductases, particularly peroxidases such as horseradish peroxidase, and the like), substrates, cofactors, inhibitors, chemiluminescent groups, chromogenic agents, and calorimetric labels such as colloidal gold or colored glass or plastic (e.g., polystyrene, polypropylene, latex, etc.) beads.

"Treat," "treating" or "treatment" as used herein refers to any type of treatment that imparts a benefit to a patient afflicted with a disease, including improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Concurrently administering" or "concurrently administer" as used herein means that the two or more compounds or compositions are administered closely enough in time to produce a combined effect (that is, concurrently may be simultaneously, or it may be two or more events occurring within a short time period before or after each other, e.g., sequentially). Simultaneous concurrent administration may be carried out by mixing the compounds prior to administration, or by administering the compounds at the same point in time but at different anatomic sites and/or by using different routes of administration.

"Internalizing factor" as used herein may be any compound or construct that binds to a cell surface protein which is then taken up into the cell by binding. Numerous such internalizing factors are known, including but not limited to those described in D. Curiel et al., U.S. Pat. Nos. 6,274,322 and 6,022,735, the disclosures of which are incorporated herein by reference.

The definitions and techniques described herein also apply to the IL-13 targeting peptides, toxin proteins, and other compounds and compositions mentioned hereinabove and hereinbelow.

B. Targeting Peptides That Bind to the Il-13 Binding Site

In some embodiments of the invention, the internalizing factor, targeting protein, peptide or agent is IL-13 or a fragment thereof that specifically binds the IL-13 receptor. The terms "peptide," "polypeptide," and "protein" are used interchangeably and refer to any polymer of amino acids (dipeptide or greater) linked through peptide bonds. Recombinant IL-13 is commercially available from a number of sources (e.g., R&D Systems, Minneapolis, Minn., and Sanofi Bio-Industries, Inc., Tervose, Pa.). Alternatively, a gene or cDNA encoding IL-13 may be cloned into a plasmid or other expression vector and expressed in any of a number of expression systems according to methods well known to those of skill in the art. Methods of cloning and expressing IL-13 and the nucleic acid sequence for IL-13 are well known (see, for example, Minty et al. (1993) supra and McKenzie (1987) supra). In addition, the expression of IL-13 as a component of a chimeric molecule is detailed below. Also contemplated is the use of specific IL-13 mutants or a fragment thereof as described in U.S. Pat. No. 6,884,603 (Debinski et al.). An exemplary IL-13 mutant is IL-13.E13K, which has an amino acid residue at position 13 substituted for lysine.

One of skill in the art will appreciate that analogues or fragments of IL-13 or IL-13 mutants will also specifically bind to the IL-13 receptor. For example, conservative substitutions of residues (e.g., a serine for an alanine or an aspartic acid for a glutamic acid) comprising native IL-13 will provide IL-13 analogues that also specifically bind to the IL-13 receptor. Thus, the terms "IL-13" or "IL-13 mutant" when used in reference to a targeting molecule, also includes fragments, analogues or peptide mimetics of IL-13 or IL-13 mutants that also specifically bind to the IL-13 receptor. Further discussion of IL-13 as contemplated by the present invention can be found in U.S. Pat. No. 5,328,984 (Pastan et al.), U.S. Pat. No. 5,614,191 (Puri et al.), U.S. Pat. No. 5,919,456 (Puri et al.), U.S. Pat. No. 6,296,843 (Debinski), U.S. Pat. No. 6,428,788 (Debinski et al.), U.S. Pat. No. 6,518,061 (Puri et al.), U.S. Pat. No. 6,576,232 (Debinski et al.), U.S. Pat. No. 6,630,576 (Debinski), and U.S. Pat. No. 6,884,603 (Debinski et al.).

In some embodiments of the present invention the targeting protein specifically binds to the IL-13Rα2 receptor. As described above the targeting protein that specifically binds to the IL-13Rα2 receptor may be IL-13, a mutant of IL-13, or a fragment thereof.

The targeting peptides of the present invention can be coupled to or conjugated to effector molecules, cytosol localization elements, or subcellular compartment localization signal elements by any suitable technique, including those described further in "Conjugates" below. The described conjugates can be used for therapeutic and/or diagnostic purposes.

C. Targeting Peptides That do not Bind to the Il-13 Binding Site

In some embodiments, the internalizing factor or targeting peptides of the present invention are not IL-13 or IL-13 mutants and/or fragments, but instead are peptides that do not bind to the IL-13 binding site, but instead bind to a different binding site on the IL-13 receptor.

The single letter code for amino acids as used herein is: A (Ala), C (Cys), D (Asp), E (Glu), F (Phe), G (Gly), H (His), I (Ile), K (Lys), L (Leu), M (Met), N (Asn), P (Pro), Q (Gln), R (Arg), S (Ser), T (Thr), V (Val), W (Trp), and Y (Tyr)).

In some embodiments, targeting peptides of the present invention can have the general formula, from amino terminus to carboxy terminus, or alternatively from carboxy terminus to aminuo terminus, of FORMULA I:

$$X—R^1—R^2—R^3—R^4—R^5—R^5—R^6—R^7—Y \qquad (I)$$

wherein:

$R^1$ is G or S;

$R^2$ is a negatively charged amino acid (for example E or D);

$R^3$ is a large hydrophobic amino acid (for example M, W, Y, or, I);

$R^4$ is a small amino acid (for example G, S or A);

$R^5$ is a large or aromatic amino acid (for example W, F, H or Y);

$R^6$ is a preferably hydrophobic or neutral amino acid (for example V, P, T or N);

$R^7$ is a positively charged amino acid (for example R, K or H); and

X and Y are as given below.

In other embodiments, targeting peptides of the present invention can have the general formula, from amino terminus to carboxy terminus, or alternatively from carboxy terminus to aminuo terminus, of FORMULA II:

$$X-R^1-R^2-R^3-R^4-R^5-R^5-R^6-R^7-Y \quad \text{(II)}$$

wherein:
R$^1$ is a hydrophobic amino acid (for example L, A, I, V, or M);
R$^2$ is a preferably hydrophobic or neutral amino acid (for example P, V, T or N);
R$^3$ is a charged or uncharged polar amino acid (for example Q, N, D, E or H)
R$^4$ is a hydrophobic amino acid (for example L, A, I, V, or M);
R$^5$ is large or aromatic amino acid (for example W, F, H or Y);
R$^6$ is a hydrophobic amino acid (for example L, A, I, V, or M);
R$^7$ is large or aromatic amino acid (for example F, W, H or Y); and
X and Y are as described below.

In still other embodiments, targeting peptides of the present invention can have the general formula, from amino terminus to carboxy terminus, or alternatively from carboxy terminus to aminuo terminus, of FORMULA III:

$$X-R^1-R^2-R^3-R^4-R^5-R^5-R^6-R^7-Y \quad \text{(III)}$$

wherein:
R$^1$ is S or G;
R$^2$ is a preferably hydrophobic or neutral amino acid (for example, P, V, T or N);
R$^3$ is large or aromatic amino acid (for example F, W, H or Y);
R$^4$ is a hydrophobic amino acid (for example, L, A, I, V, or M);
R$^5$ is large or aromatic amino acid (for example H, W, F, or Y);
R$^6$ is a hydrophobic amino acid (for example L, A, I, V, or M);
R$^7$ is a hydrophobic amino acid (for example L, A, I, V, or M); and
X and Y are as described below.

In Formulas I-III, X and Y can each independently be present or absent and when present can each independently be a capping group, a linking group (or "linker", including non-amino acid linking groups, see, e.g., U.S. Pat. Nos. 7,468,418; 7,402,652; and 7,351,797), an amino acid (e.g. C, S or G) optionally terminated by a capping group or linking group, or a peptide consisting of from 2 to 6 or 10 additional amino acids optionally terminated by a capping group or linking group.

The amino acids of peptides of the invention may be in D form, L form, or a combination thereof.

Specific examples of targeting peptides of FORMULAS I-III include, but are not limited to those set forth in Tables 1-3 and Tables 4-6 below. These peptides may or may not have linking groups bonded to the carboxy terminus. Linking groups as used herein are described in more detail below.

Active compounds of the present invention can be produced by any suitable means, including by synthetic organic chemical techniques or by recombinant techniques in which a nucleic acid that encodes the active compound is produced and introduced into a host cell (typically in the form of an expression vector) so that the encoded active compound (peptide, fusion peptide, etc.) is expressed therein. Expression vectors can be designed for expression of proteins or polypeptides in prokaryotic or eukaryotic cells. For example, polypeptides can be expressed in bacterial cells such as *E. coli*, insect cells (e.g., in the baculovirus expression system), yeast cells or mammalian cells. Suitable host cells are discussed further in Goeddel, Gene Expression Technology: Methods in Enzymology 185, Academic Press, San Diego, Calif. (1990). Examples of vectors for expression in yeast *S. cerevisiae* include pYepSec1 (Baldari et al, (1987) EMBO J. 6:229-234), pMFa (Kurjan and Herskowitz (1982) Cell 30:933-943), pJRY88 (Schultz et al. (1987) Gene 54:113-123), and pYES2 (Invitrogen Corporation, San Diego, Calif.). Baculovirus vectors available for expression of nucleic acids to produce proteins in cultured insect cells (e.g., Sf 9 cells) include the pAc series (Smith et al. (1983) Mol. Cell. Biol. 3:2156-2165) and the pVL series (Lucklow & Summers (1989) Virology 170:31-39).

Vectors can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al. (Molecular Cloning: A Laboratory Manual, 2nd Edition, Cold Spring Harbor Laboratory press (1989)), and other laboratory manuals.

TABLE 1

Peptides of Formula I

| | |
|---|---|
| CGEMGWVRC; and | (SEQ ID NO: 1) |
| ACGEMGWVRCGGGS. | (SEQ ID NO: 2) |

TABLE 2

Peptides of Formula II

| | |
|---|---|
| CLPQLWLFC; | (SEQ ID NO: 3) |
| ACLPQLWLFCGGGS; | (SEQ ID NO: 4) |

TABLE 3

Peptides of Formula III

| | |
|---|---|
| CSPFLHLLC; and | (SEQ ID NO: 5) |
| ACSPFLHLLCGGGS. | (SEQ ID NO: 6) |

TABLE 4

Additional Peptides of Formula I

| | |
|---|---|
| SEMGWVRC | (SEQ ID NO: 7) |
| GDMGWVR | (SEQ ID NO: 8) |
| SDWGWVR | (SEQ ID NO: 9) |

TABLE 4-continued

Additional Peptides of Formula I

| | |
|---|---|
| GDYGWVR | (SEQ ID NO: 10) |
| SEIGWVR | SEQ ID NO: 11) |
| GEISWVR | (SEQ ID NO: 12) |
| GEMAWVR | (SEQ ID NO: 13) |
| GEMGFVR | (SEQ ID NO: 14) |
| GEMGHVR | (SEQ ID NO: 15) |
| GEMSYVR | (SEQ ID NO: 16) |
| GEMGWPR | (SEQ ID NO: 17) |
| GEMGWTR | (SEQ ID NO: 18) |
| GEMGWNK | (SEQ ID NO: 19) |
| GEMGWNH | (SEQ ID NO: 20) |

TABLE 5

Additional Peptides of Formula II

| | |
|---|---|
| APQLWLF | (SEQ ID NO: 21) |
| IPQLWLF | (SEQ ID NO: 22) |
| VPQLWLF | (SEQ ID NO: 23) |
| MPQLWLF | (SEQ ID NO: 24) |
| LVQLWLF | (SEQ ID NO: 25) |
| LTQLWLF | (SEQ ID NO: 26) |
| LNQLWLF | (SEQ ID NO: 27) |
| LPNLWLF | (SEQ ID NO: 28) |
| LPDLWLF | (SEQ ID NO: 29) |
| LPELWLF | (SEQ ID NO: 30) |
| LPHLWLF | (SEQ ID NO: 31) |
| LPQAFAW | (SEQ ID NO: 32) |
| LPQIFIH | (SEQ ID NO: 33) |
| LPQVHVY | (SEQ ID NO: 34) |
| LPQMYMY | (SEQ ID NO: 35) |
| MNHMYMY | (SEQ ID NO: 36) |
| VTEVHVH | (SEQ ID NO: 37) |

TABLE 6

Additional Peptides of Formula III

| | |
|---|---|
| GPFLHLL | (SEQ ID NO: 38) |
| SVFLHLL | (SEQ ID NO: 39) |
| STFLHLL | (SEQ ID NO: 40) |
| SNWLHLL | (SEQ ID NO: 41) |

TABLE 6-continued

Additional Peptides of Formula III

| | |
|---|---|
| SPHLHLL | (SEQ ID NO: 42) |
| SPYLHLL | (SEQ ID NO: 43) |
| SPFAHLL | (SEQ ID NO: 44) |
| SPFIHLL | (SEQ ID NO: 45) |
| SPFVHLL | (SEQ ID NO: 46) |
| SPFMHLL | (SEQ ID NO: 47) |
| SPFLWLL | (SEQ ID NO: 48) |
| SPFLFAA | (SEQ ID NO: 49) |
| SPFLFII | (SEQ ID NO: 50) |
| SPFLHVV | (SEQ ID NO: 51) |
| SPFLYMM | (SEQ ID NO: 52) |
| GNYMYMM | (SEQ ID NO: 53) |
| GTHVFVI | (SEQ ID NO: 54) |

D. Conjugates

Targeting peptides as described herein may be coupled to or conjugated to an effector molecule such as a diagnostic and/or therapeutic agent in accordance with any of a variety of techniques, such as those employed in the production of immunoconjugates. See, e.g., U.S. Pat. No. 6,949,245 to Sliwkowski.

In some embodiments, recombinant fusion chimera protein anti-cancer cytotoxins are composed of a carrier/ligand and an effector (catalyst). Carrier/ligands can be proteinaceous compounds, such as growth factors, cytokines, and monoclonal antibodies, Among effectors, bacterial toxins, such as *Pseudomonas* exotoxin A and Diphtheria toxin, or plant toxins, such as ricin may be utilized in some embodiments. The fusion protein is targeted only to cells expressing a target receptor/adaptor for a carrier/ligand. These targets internalize in response to carrier/ligand binding. Targets include, but are not limited to, protein receptors, antigens of various nature, adhesion molecules, gangliosides, etc. For example, EphA2 is over-expressed in a majority of patients with GBM and its ligand induces a receptor-mediated internalization once it binds the receptor (Walker-Daniels et al. (2002) Mol. Cancer. Res. 1:79-87). The latter may be used for, e.g., recombinant bacterial toxin-containing cytotoxins to exert anti-tumor action (Debinski (2002) Molecular "Targeting of Brain Tumors with Cytotoxin," In: Chimeric Toxins (Lorberboum-Galski & Lazarovici, eds., Harwood Academic Publishers) pp. 222-246; Debinski (2002) Cancer Invest. 20:801-809; Debinski (2002) Cancer Invest. 20:801-809). Another non-limited example is the IL-13Rα2 receptor whose ligand is internalized through receptor mediated endocytosis.

Chemotherapeutic agents useful in the generation of such active compounds include those described above. Conjugates of targeting peptide and one or more small molecule toxins, such as a calicheamicin, a maytansine (See U.S. Pat. No. 5,208,020), a trichothene, and CC 1065 are also contemplated herein. In some embodiments, conjugates of targeting peptide to *Pseudomonas* exotoxins are used (U.S. Pat. No. 5,328,984 to Pastan et al.).

In some embodiments of the invention, the targeting peptide conjugated to one or more maytansine molecules (e.g., about 1 to about 10 maytansine molecules per targeting peptide molecule). Maytansine may, for example, be converted to May-SS-Me which may be reduced to May-SH3 and reacted with modified targeting peptide (Chari et al. (1992) Cancer Res. 52: 127-131) to generate an active compound.

Another conjugate of interest includes a targeting peptide conjugated to one or more calicheamicin molecules. The calicheamicin family of antibiotics is capable of producing double-stranded DNA breaks at sub-picomolar concentrations. Structural analogues of calicheamicin that may be used include, but are not limited to, $\gamma_1^1$, $\alpha_2^1$, $\alpha_3^1$, N-acetyl-$\gamma_1^1$, PSAG and $\theta_1^1$, (Hinman et al. (1993) Cancer Res. 53:3336-3342; Lode et al. (1998) Cancer Res. 58:2925-2928). See also U.S. Pat. Nos. 5,714,586, 5,712,374, 5,264,586, and 5,773,001.

Enzymatically active toxins and fragments thereof which can be used are described above and include diphtheria A chain, nonbinding active fragments of diphtheria toxin, exotoxin A chain (from *Pseudomonas aeruginosa*), ricin A chain, abrin A chain (from *Corrybacterium typhimuriae*), modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates a conjugate formed between active compounds and an antibody or a compound with nucleolytic activity (e.g., a ribonuclease or a DNA endonuclease such as a deoxyribonuclease; DNase).

A variety of radioactive isotopes or radionuclides are available for the production of radioconjugated compounds as described above.

In some embodiments, conjugates of a targeting agent and therapeutic agents or detectable groups may be made using a variety of bi-functional protein coupling agents such as N-succinimidyl-3-(2-pyridyldithiol)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin conjugate can be prepared as described in Vitetta et al. (1987) Science 238:1098. Carbon-14-labeled 1-isothiocyanatobenzyl-3-methyldiethylene triaminepentaacetic acid (MX-DTPA) is an exemplary chelating agent for conjugation of radionucleotide to the targeting peptide. See WO 94/11026. The linker may be a "cleavable linker" facilitating release of the cytotoxic drug in the cell. For example, an acid-labile linker, peptidase-sensitive linker, dimethyl linker or disulfide-containing linker (Chari et al. (1992) Cancer Res. 52:127-131) may be used.

Alternatively, a fusion protein including the targeting agent and therapeutic agent or detectable group may be made, e.g. by recombinant techniques or peptide synthesis.

In yet another embodiment, the targeting agent may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

In some embodiments, the targeting peptide is fused to a *Pseudomonas* exotoxin or Diphtheria toxin. (U.S. Pat. No. 5,328,984 to Pastan et al. and U.S. Pat. No. 6,296,843 to Debinski). *Pseudomonas* exotoxins include, but are not limited to, *Pseudomonas* exotoxin A (PE). The *Pseudomonas* exotoxin can be modified such that it substantially lacks domain Ia, and *Pseudomonas* exotoxins may further include PE38QQR and PE4E. Diphtheria toxins include DT390, a diphtheria toxin in which the native binding domain is eliminated. It will be appreciated that the toxin can be connected to either of the amino terminus, or the carboxyl terminus.

The present invention further contemplates a fusion protein comprising, consisting of, or consisting essentially of the targeting protein and a cytosol localization element, which can be made by, for example, recombinant techniques or peptide synthesis. In some embodiments this fusion protein also comprises, consists of, or consists essentially of an effector molecule.

"Cytosol localization element" (also referred to as an endosomal exit element) as used herein refers to an amino acid sequence used to direct a target protein, fusion protein, or fragment thereof to the cytoplasm. The amino acid sequence can be of any size and composition, for example 3 to 100 amino acids in length to, 4, 5, 6, 7, 8, 10, 12, 15, 20, 25, 30, 40, 50, 60, 70, 80, 90 or 100 amino acids in length. In some embodiments the cytosol localization element enables the fusion protein or a fragment thereof to exit an endocytic compartment after being internalized in the process of receptor-mediated internalization and enter the cytoplasm. In some embodiments the cytosol localization element is proteolytically activated, such as, but not limited to, by a calcium-dependent serine endoprotease, such as furin. Exemplary cytosol localization elements include, but are not limited to cytosol localization elements of bacterial toxins. Such bacterial toxins include, but are not limited to *Pseudomonas* exotoxin A (PE), Diphtheria toxin (DT), and Ricin A chain. Additional examples are described in: B. Beaumelle et al., Selective translocation of the A chain of Diphtheria toxin across the membrane of purified endosomes. I *Biol. Chem.* 267:11525-11531 (1992); I. Madshus et al., Membrane translocation of Diphtheria toxin carrying passenger protein domain, *Inf. Immun.* 60:3296-3302 (1992); H. Stenmark et al., Peptides fused to the amino-terminal end of Diphtheria toxin are translocated to the cytosol, *J. Cell Biol.* 113:1025-1032 (1991); and R. Chignola et al., Self-potentiation of ligand-toxin conjugates containing Ricin A chain fused with viral structures, *J Biol Chem* 270:23345-23351 (1995). Still other exemplary cytosol localization elements include those describe in U.S. Pat. No. 6,235,526, which is incorporated herein by reference.

The present invention further contemplates a fusion protein comprising, consisting of, or consisting essentially of the targeting protein and a subcellular compartment localization signal element, which can be made by, for example, recombinant techniques or peptide synthesis. In some embodiments this fusion protein also comprises, consists of, or consists essentially of a cytosol localization element and optionally an effector molecule.

"Subcellular compartment localization signal element" as used herein refers to a signal sequence or tag used to direct a target protein, fusion protein, or fragment thereof to particular cellular organelles. In some embodiments the subcellular compartment localization signal element comprises a peptide sequence. Such peptide sequences can be of any size and composition, for example 3 to 100 amino acids in length to, 4, 5, 6, 7, 8, 10, 12, 15, 20, 25, 30, 40, 50, 60, 70, 80, 90 or 100 amino acids in length. Exemplary cellular organelles include, but are not limited to, the nucleus, endoplasmic reticulum, golgi apparatus, endosomes, lysosomes, peroxisomes and mitochondria. Various subcellular compartment localization signal elements are known and/or commercially available. Exemplary subcellular compartment localization signal elements include, but are not limited to, nuclear localization signals and lysosomal localization signals. Other exemplary subcellular compartment localization signal elements include those described in U.S. Pat. No. 7,585,636, which is incorporated herein by reference.

"Nuclear localization signals" as used herein refers to an amino acid sequence which directs a target protein, fusion protein, or fragment thereof into the nucleus of a cell. Generally, nuclear localization signals (NLS) are a class of short amino acid sequences which may be exploited for cellular import of linked or coupled cargo into the nucleus. Such amino acid sequences can be from 3 to 100 amino acids in length to 3 to 50, 4 to 30, or 4 to 20 amino acids in length. The nuclear localization sequences of the present invention can be: (i) a monopartite nuclear localization sequence exemplified by the SV40 large T antigen NLS (PKKKRKV) (SEQ ID NO: 55); (ii) a bipartite motif consisting of two basic domains separated by a variable number of spacer amino acids and exemplified by the *Xenopus* nucleoplasmin NLS (KRXXXXXXXXXXKKKL) (SEQ ID NO: 56); or (iii) non-canonical sequences such as M9 of the hnRNP A1 protein, the influenza virus nucleoprotein NLS, and the yeast Gal4 protein NLS (Dingwall and Laskey, Trends Biochem Sci 16:478-481, 1991). In some embodiments, the nuclear localization signal is a highly cationic or basic peptide. In other embodiments the NLS comprises two or more Arg or Lys amino acid residues. In further embodiments of the present invention the NLS sequence binds to cytosolic proteins, such as importins and karyopherins, which recognize and transport NLS-containing proteins or peptides to the nuclear pore complex. The present invention envisions the use of any nuclear localization signal peptide, including but not limited to, SV40 virus T-antigen NLS and NLS sequences domain derived from viral Tat proteins, such as HIV Tat. Other exemplary nuclear localization signals include, but are not limited to those discussed in Cokol et al., 2000, EMBO Reports, 1(5):411-415, Boulikas, T., 1993, Crit. Rev. Eukaryot. Gene Expr., 3:193-227, Collas, P. et al., 1996, Transgenic Research, 5: 451-458, Collas and Alestrom, 1997, Biochem. Cell Biol. 75: 633-640, Collas and Alestrom, 1998, Transgenic Research, 7: 303-309, Collas and Alestrom, 1996, Mol. Reprod. Devel., 45:431-438, and U.S. Pat. Nos. 7,531,624, 7,498,177, 7,332,586, and 7,550,650, all of which are incorporated by reference in their entireties.

"Lysosomal localization signal" as used herein refers to an amino acid sequence which directs a target protein or fusion protein to lysozymes. Examples include, but are not limited to, lysosome associated membrane protein 1 (LAMP-1) tail sequence: RKRSHAGYQTI (SEQ ID NO: 57); lysosomal acid phosphatase (LAP): RLKRMQAQPPGYRH-VADGEDHAV (SEQ ID NO: 58), and lysosomal integral membrane protein 2 (LIMP-2): RGQGSTDEGTADERAP-LIRT (SEQ ID NO: 59).

In some embodiments of the present invention the fusion protein comprises, consists of, or consists essentially of a targeting protein, a cytosol localization element, a subcellular compartment localization signal element, and optionally an effector molecule. These components may be coupled to one another in any order that allows for the targeting protein to bind to its receptor and further allows for the transport of the fusion protein or a fragment thereof into the nucleus.

In further embodiments of the present invention the fusion protein comprises, consists of, or consists essentially of a targeting protein comprising IL-13, a mutant of IL-13 or an analogue or fragment thereof; a cytosol localization element comprising *Pseudomonas* exotoxin A (PE) or Diphtheria toxin (DT); and a subcellular compartment localization signal element comprising a nuclear localization signal or a lysosomal localization signal. In other embodiments of the present invention the fusion protein comprises, consists of, or consists essentially of IL-13.E13K, the cytosol bacterial toxin domain D2 of PE, and a nuclear localization signal from the SV40 T antigen. In one embodiment of the present invention the fusion protein is a single-chain recombinant protein comprising, consisting of, or consisting essentially of, from the N-terminus to the C-terminus, IL-13.E13K, the cytosol bacterial toxin domain D2 of PE, and a nuclear localization signal from the SV40 T antigen, i.e. IL-13.E13K-D2-NLS.

E. Pharmaceutical Formulations and Methods

The active compounds, conjugates, and/or compositions thereof described herein may be formulated for administration in a pharmaceutical carrier in accordance with known techniques. See, e.g., Remington, *The Science and Practice of Pharmacy* ($9^{th}$ Ed. 1995). In the manufacture of a pharmaceutical formulation according to the invention, the active compound(s) (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound(s) as a unit-dose formulation, for example, a tablet, which may contain from 0.01 or 0.5% to 95% or 99% by weight of the active compound. One or more active compounds may be incorporated in the formulations of the invention, which may be prepared by any of the well-known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Particular routes of parenteral administration include intrathecal injection, including directly into the tumor or a tumor resection cavity, and intraventricular injection into a ventricle of the brain.

Active compounds and compositions may be administered by intratumor injection (including tumors in any region such as tumors of the brain), or in the case of brain tumors injection into a ventricle of the brain.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes that render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound or composition in a unit dosage form in a sealed container. The compound or composition is provided in the form of a lyophilizate that is capable of being reconstituted with a suitable pharmaceutically acceptable carrier to form a liquid composition suitable for injection thereof into a subject. The unit dosage form typically comprises from about 10 mg to about 10 grams of the compound or composition. When the compound or composition is substantially water-insoluble, a sufficient amount of emulsifying agent that is physiologically acceptable may be employed in sufficient quantity to emulsify the compound or composition in an aqueous carrier. One such useful emulsifying agent is phosphatidyl choline.

Further, the present invention provides liposomal formulations of the compounds disclosed herein and compositions thereof. The technology for forming liposomal suspensions is well known in the art. When the compound or composition thereof is an aqueous-soluble composition, using conventional liposome technology, the same may be incorporated into lipid vesicles. In such an instance, due to the water solubility of the compound or composition, the compound or composition will be substantially entrained within the hydrophilic center or core of the liposomes. The lipid layer employed may be of any conventional composition and may either contain cholesterol or may be cholesterol-free. When the compound or composition of interest is water-insoluble, again employing conventional liposome formation technology, the composition may be substantially entrained within the hydrophobic lipid bilayer that forms the structure of the liposome. In either instance, the liposomes that are produced may be reduced in size, as through the use of standard sonication and homogenization techniques.

Liposomal formulations containing the compounds disclosed herein or compositions thereof (e.g., IL-13 conjugates, such as IL-13.E13K-D2-NLS), may be lyophilized to produce a lyophilizate, which may be reconstituted with a pharmaceutically acceptable carrier, such as water, to regenerate a liposomal suspension. Examples of liposomal formulations that can be used include the neutral lipid 1,2-dioleoyl-sn-glycero-3-phosphatidylcholine (DPOC) (See, e.g., Landen Jr. et al. (2005) Cancer Res. 65:6910-6918).

Other pharmaceutical compositions may be prepared from the water-insoluble compounds disclosed herein, or compositions thereof, such as aqueous base emulsions. In such an instance, the composition will contain a sufficient amount of pharmaceutically acceptable emulsifying agent to emulsify the desired amount of the compound or composition thereof. Particularly useful emulsifying agents include phosphatidyl cholines, and lecithin.

In addition to active compounds, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well-known in the art.

The therapeutically effective dosage of any one active agent, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art.

As a general proposition, the initial pharmaceutically effective amount of the active compound or composition administered parenterally will be in the range of about 0.1 to 50 mg/kg of patient body weight per day, with the typical initial range of antibody used being 0.3 to 20 mg/kg/day, more preferably 0.3 to 15 mg/kg/day. The desired dosage can be delivered by a single bolus administration, by multiple bolus administrations, or by continuous infusion administration of active compound, depending on the pattern of pharmacokinetic decay that the practitioner wishes to achieve.

The active compound(s) is suitably administered to the patient at one time or over a series of treatments. Depending on the type and severity of the disease, about 1 µg/kg to 15 mg/kg (e.g. 0.1-20 mg/kg) of active compound(s) is an initial candidate dosage for administration to the patient, whether, for example, by one or more separate administrations, or by continuous infusion. A typical daily dosage might range from about 0.1, 0.5, 1, 10 or 100 µg/kg up to 100, 200 or 500 mg/kg, or more, depending on the factors mentioned above. For repeated administrations over several days or longer, depending on the condition, the treatment is sustained until a desired suppression of disease symptoms occurs. A more particular dosage of the active compound will be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g., such that the patient receives from about two to about twenty, e.g. about six doses of the anti-ErbB2 antibody). An initial higher loading dose, followed by one or more lower doses may be administered. An exemplary dosing regimen comprises administering an initial loading dose of about 0.5 to 10 mg/kg, followed by a weekly maintenance dose of about 0.5 to 10 mg/kg of the active compound. However, other dosage regimens may be useful. The progress of this therapy is easily monitored by conventional techniques and assays.

Subjects treated by the methods of the present invention can also be administered one or more additional therapeutic agents. See U.S. Pat. No. 5,677,178. Chemotherapeutic agents may be administered by methods well known to the skilled practitioner, including systemically, direct injection into the cancer, or by localization at the site of the cancer by associating the desired chemotherapeutic agent with an appropriate slow release material or intra-arterial perfusing of the tumor. The preferred dose may be chosen by the practitioner based on the nature of the cancer to be treated, and other factors routinely considered in administering. See, e.g., U.S. Pat. No. 7,078,030.

Subjects may also be treated by radiation therapy, including, but not limited to, external beam radiotherapy, which may be at any suitable dose (e.g., 20 to 70 Gy or more per tumor, typically delivered over a fractionated schedule).

Pharmaceutical compositions containing targeting agent in unlabeled form may be administered to subjects as blocking reagents, in like manner as described in Abrams et al., U.S. Pat. No. RE38,008, in conjunction with the administration of targeting agent coupled to a therapeutic group.

Targeting peptide coupled to a diagnostic group may also be used in vitro as histological reagents on tissue samples, where binding of the IL-13 receptor is indicative of cancer tissue in the tissue sample.

EXAMPLES

Materials and Methods

Cell Culture.

Human GBM cell lines U-251 MG and LN229 were obtained from American Type Culture Collection (Manassas, Va.). U-251 MG cells were maintained in DMEM (Lonza, Walkersville, Md.) supplemented with 1× non-essential amino acid (Invitrogen, Carlsbad, Calif.) and 10% FCS (Hyclone, Logan, Utah). LN229 cells were grown in DMEM supplemented with 10% FCS. G48a cells were grown and maintained in RPMI 1640 (Lonza, Walkersville, Md.) supplemented with glucose, adjusted to 4 gm/liter of media and 10% FCS (13).

Cloning, Production and Purification of Targeted Proteins.

A duplex primer cloning strategy was employed wherein SV40 T-antigen NLS 5' and 3' sequence primers were synthesised (Invitrogen) and made into duplex DNA (containing Xho1/BamH1 ends) by incubating the primers in favorable annealing conditions. The annealed duplex was then subcloned into the IL-13-D2 containing plasmid using Xho1/BamH1 at the 3' end to produce IL-13-D2-NLS. The IL-13-D2 plasmid was engineered by sub-cloning it from a previously generated IL-13-D2-PE38QQR plasmid (24). The IL-13 mutant recombinant constructs were made by replacing the wild type IL-13 sequence from the parent plasmid with the mutant IL-13 sequence (25). The NH2-terminal end of NLS domain was joined to the COOH terminal of IL-13.E13K domain using the HindIII site to form the IL-13.E13K-NLS plasmid. Also, all of these recombinant constructs were transformed in DH5α $E.$ $coli$ cells for amplification. All the constructs were sequenced at DNA sequencing Laboratory of the Comprehensive Center of Wake Forest University and analyzed for their in-frame DNA sequence using an automated sequence analyzer prior to protein expression.

Also, the IL-13/IL-13.E13K-D2-NLS and other control DNA constructs have been created in a manner such that it enables the expression of these proteins under the IPTG inducible T7 promoter in BL21 (λDE3) $E.$ $coli$ protein expression system as previously described (33). In brief, the recombinant constructs were transformed in BL21 cells and the cells were grown in Luria-broth media supplemented with 100 μg/ml of ampicillin at 37° C. shaker. When the A600 of the bacterial culture media reached around 1.4, the recombinant protein expression in the cells was induced by addition of 1 nmol/L of IPTG and allowed to incubate for further 90 min. The expressed proteins in the inclusion bodies were then denatured using 7 M Guanidine (MP Biomedicals, Salon, Ohio) and 1,4-Dithiothr.eitol (Sigma, St. Louis, Mo.). The reduced protein was then renatured in a buffer containing arginine/L-glutathione oxidase (Sigma, St. Louis, Mo.). The protein was further dialyzed and purified by SP Sepharose ion-exchange liquid chromatography (GE Healthcare, Piscataway, N.J.) using Fast Protein Liquid Chromatography system (GE Healthcare, Piscataway, N.J.). The purified proteins were subsequently run on SDS-PAGE gels to identify the purity of the isolated proteins. All the proteins obtained were >90% pure.

Colorimetric MTS/PMS Cell Viability Assay.

$1 \times 10^3$ U-251 MG cells were plated per well in quadruplicates for each concentration to be tested. IL-13.E13K-PE38QQR is an IL-13Rα2 based cytotoxin against GBM (24). After 24 hours incubation at 37° C. for the cells to attach, a fixed concentration (i.e. 1 μM) of the IL13.E13K-D2-NLS and other purified proteins were added and incubated at 37° C. for 1 hr. After 1 hr. incubation, increasing concentrations of the IL-13.E13K-PE38QQR ranging from 0.1 to 100 ng/ml was added and the plate was incubated for 48 hr. Cells treated with cyclohexamide and just the cytotoxins were used as controls. After 48 hr., cell viability was measured using the MTS [3-(4,5-dimethylthiazol-2-yl)-5-(3-carboxymethoxyphenyl)-2-(4-sulfophenyl)-2H-tetrazolium] PMS [phenazine methosulfate] dye (Promega, Madison, Wis.) as per the manufacturer's instructions. The absorbance from the assay was measured at 490 nm using the plate reader Spectra max 340 PC (Molecular Devices, Sunnyvale, Calif.) and data was plotted as percentage of control versus concentration of the toxin used.

IL-13-D2-NLS and IL-13-D2 Labeling with EDC-Sulpho-NHS and Alexa Fluor 488 Labels.

Purified IL-13-D2-NLS and the IL-13-D2 proteins were labeled at their carboxylate amino acids via EDC (1-ethyl-3-[3-dimethylaminopropyl]carbodiimide hydrochloride). EDC reacts with a carboxyl group on an amino acid of the protein and forms an amine reactive O-acylisourea intermediate that swiftly reacts with an amino group to form an amide bond and release the isourea by-product. The intermediate is unstable in aqueous solutions and therefore, two-step conjugation procedures require N-hydroxysuccinimide stabilization (Sulfo-NHS). Sulfo-NHS reacts with the O-acylisourea intermediate and stabilizes it. Next, Alexa fluor 488-hydrazide was added, which replaced the Sulfo-NHS and formed a stable amide bond on the carboxyl groups of the protein to form labeled protein conjugates.

The proteins were initially dissolved in the activation buffer (0.05 M MES, 0.5 M NaCl, pH 6) at the concentration of 1 mg/ml using buffer-exchange columns. Later 2 mM EDC and 5 mM Sulfo-NHS (Thermo Scientific, Waltham, Mass.) were added to the proteins and allowed to react for 15 min at RT. Subsequently, 0.14 μl of 2-mercaptoethanol was added to quench the unreacted EDC. The protein-EDC-Sulfo-NHS conjugates were then dissolved in the coupling buffer (0.1 M sodium phosphate, 0.15 M NaCl, pH 7.5) using buffer exchange columns (Pierce, Rockford, Ill.). Next, alexa fluor 488 hydrazide (dissolved in the coupling buffer) (Invitrogen, Carlsbad, Calif.) was added at 25 molar concentration excess to the proteins and incubated in the dark at RT for 30 minutes. After incubation, 10 mM hydroxylamine (Thermo Scientific, Rockford, Ill.) was added to quench the excess fluor. The excess unreacted hydrazide fluor was removed using Pierce protein desalting columns.

Localization Studies of the Labeled Proteins on IL-13Rα2 Positive U-251 MG Cells Using Alexa Fluor 488 EDC-Sulfo-NHS Labeled Proteins.

25,000 U-251 MG GBM cells were plated on coverslip/per well in a 24-well plate. The cells were allowed to adhere to the coverslips for 24 hr., after which 500 nM each of the EDC-Sulpho-NHS labeled proteins were added to the U-251 MG cells for 15 min and 4 hr. After the incubations, the cells were fixed with acetone (pre-chilled at −20° F.) for 10 mins and washed with PBS 4× times. The coverslips were then mounted on the slides using the gel mount (Biomeda, Foster City, Calif.) and observed with LSM 510 Zeiss Confocal Microscope (Cellular Imaging Core, Comprehensive Cancer Center, Wake Forest University) and the images processed using Zeiss LSM Image Browser (version 4.2).

Direct Labeling of IL-13.E13K-D2-NLS and IL-13.E13K-D2 with Alexa Fluor Labels.

The proteins were directly labeled with alexa fluor 488 dye using the Alexa fluor 488 microscale protein labeling kit from Invitrogen (Carlsbad, Calif.) as per the manufacturer's instructions. A molar ratio of 25 of the dye to the protein was used to label both the proteins. The proteins were run on 12% SDS-PAGE gel. The gel was scanned using Typhoon 9210 (Amersham Pharmacia Biotech) for fluorescence signals and later stained using coomassie blue dye.

Localization Studies of the Labeled Proteins on IL-13Rα2 Positive U-251 MG Cells for Alexa Fluor 488 Directly Labeled Proteins.

25,000 U-251 MG GBM cells were plated on coverslips per well in a 24-well plate. After 24 hr. for allowing the cells to adhere and attach to the plate, 1 µM/well of alexa fluor directly labeled proteins were added to the U-251 MG cells for 15 min and 4 hr. After the incubations, the cells were fixed with 5% paraformaldehyde (Ted Pella, Redding, Calif.) for 15 mins at 37° C. and washed with 1×PBS (3 times). The cells were then permeabilized with 0.1% Triton-X-100/0.2% BSA-PBS for 10 mM at RT. After permeabilization, the cells were washed 3 times with 1×PBS. Subsequently, Topro-3 iodide (Invitrogen, Carlsbad, Calif.) was added at a concentration of 1:1000 dilution of the 1 mM stock to stain the cell nuclei. The coverslips were then mounted on the slides using the gel mount (Biomeda, Foster City, Calif.) and observed with LSM 510 Zeiss Confocal Microscope (Cellular Imaging Core, Comprehensive Cancer Center, Wake Forest University) and the images processed using Zeiss LSM Image Browser (version 4.2).

Direct Labeling of IL-13.E13K-D2-NLS and IL-13.E13K-D2 with Biotin and Tyramide Signal Amplification System.

Biotin-XX microscale protein labeling kit (Invitrogen, Carlsbad, Calif.) was used to label the proteins as per the manufacturer's instructions. A different molar ratio of 12, 8 or 4 biotin-dye to the proteins was used. The biotin-labeled proteins were run on a gel and a western blot carried out using streptavidin-HR.P (Pierce, Rockford, Ill.) to detect for biotin-labeled proteins. The number of Biotin molecules attached to the proteins was determined by the Biofluoreporter assay kit (Invitrogen) as per the manufacturer's guidelines.

Localization Studies of the Labeled Proteins on IL-13Rα2 Positive U-251 MG Cells for Biotin-Conjugated Proteins.

12,500 U-251 MG GBM cells were plated on coverslips per well in a 24-well plate. After 24 hr., 1 µM/well of biotin-labeled proteins was added onto the U-251 MG cells for 15 min, 4, 8 and 24 hr. After the incubations, the cells were fixed with 4% paraformaldehyde (Ted Pella, Redding, Calif.) for 15 mins at 37° C. and washed with PBS 4× times. The cells were then permeabilized with 0.1% Triton-X-100/0.2% BSA-PBS for 10 min at RT. After permeabilization, the cells were washed 3 times with 1×PBS. After washings, Tyramide signal amplification kit (Invitrogen, Carlsbad, Calif.) using Alexa fluor 488 dyes and HR.P-streptavidin was carried out as per manufacturer's instructions. Topro-3 iodide (Invitrogen, Carlsbad, Calif.) was added at a concentration of 1:1000 dilution of the 1 mM stock to stain the cell nuclei. After the tyramide staining, wells were washed and mounted with gel mount (Biomeda, Foster City, Calif.) and observed with LSM 510 Zeiss Confocal Microscope (Cellular Imaging Core, Comprehensive Cancer Center, Wake Forest University) and the images processed using Zeiss LSM Image Browser (version 4.2).

Immunoblotting.

500 ng/well of each of the recombinant biotin conjugated proteins were loaded onto a 12% SDS-PAGE gel and transferred to a polyvinylidene difluoride membrane (Perkin Elmer, Shelton, Conn.). Blots were blocked with 5% milk-phosphate buffered saline (PBS) for 1 hr. at room temperature (RT). Biotin-proteins were detected using streptavidin conjugated with horseradish peroxidase (Thermo Fisher Scientific, Rockford, Ill.) diluted 1:16000 in blocking buffer. The detection was performed using an ECL plus kit (GE Healthcare).

Results

Production of IL-13.E13K-D2-NLS, IL-13.E13K-D2, IL-13.E13K-NLS and IL-13.E13K Proteins.

We aim at developing effective drug/radioactive isotope delivery vehicles to specific intracellular compartments of a cancer cell, based preferentially on recombinant proteins. Hence, we have developed here a recombinant protein delivery vehicle to the nuclei of GBM cells. This delivery vehicle recognizes the IL-13Rα2, which is overexpressed on GBM cells. The IL-13.E13K-D2-NLS recombinant protein recognizes IL-13Rα2 and is internalized into the GBM cells, exits endosomes and is trafficked to the cell's nuclei. IL-13.E13K-D2-NLS and its control proteins, IL-13.E13K-NLS and IL-13.E13K-D2 as well as IL-13.E13K, which are not expected to either leave the endosomal compartment or reach the nucleus, respectively were produced in E. coli and purified using the FPLC system. IL-13.E13K-D2-NLS was highly inducible in BL21 E. coli cells. The induced protein was isolated and further processed using a disulphide-shuffling method and purified using FPLC column, as described previously (25; 34). Even with the first step of purification, the protein was highly purified. The control IL-13.E13K-D2, the IL-13.E13K-NLS and the IL-13.E13K recombinant proteins were expressed, processed and purified in a similar manner.

IL-13.E13K-D2-NLS, IL-13.E13K-D2, IL-13.E13K-NLS and IL-13.E13K Compete for IL-13Rα2 on GBM Cells.

We next wished to confirm that all the purified recombinant proteins bind to the IL-13Rα2 receptor on GBM cells. To this end, we carried out a cell-viability assay in which these recombinant proteins bound to the IL-13Rα2 receptor and protected against cytotoxic action of IL-13.E13K-PE38QQR. IL-13.E13K-PE38QQR, as mentioned earlier, is a recombinant cytotoxin that binds to the IL-13Rα2, is internalized into cells leading to cell killing through the cleaved active portion of PE, enzymatic domain III. As expected, all recombinant proteins of interest blocked the action of the cytotoxin, resulting in no cell killing: IL13.E13K-D2-NLS; IL-13.E13K-D2; IL-13.E13K-NLS and IL-13.E13K. These results confirm that all the recombinant proteins retain IL-13.E13K ligand binding properties and compete specifically for the IL-13Rα2.

IL-13.E13K-D2-NLS Localizes to the Nuclei of U-251 MG GBM Cells.

Next, we wished to monitor the intracellular journey as well as the subcellular localization of our targeted proteins. To this end, we fluorescently labeled these proteins using three different approaches/methods. For the first approach, we labeled the carboxyl amino acids of the proteins, so as not to modify the primary amines (lysines) present in the NLS domain of the protein. Thus, we utilized the Sulfo-NHS-EDC and Alexa fluor 488 labeling techniques. IL-13-D2-NLS and IL-13-D2 were labeled at their carboxylate groups on amino acids with alexa fluor 488 via EDC (1-ethyl-3-[3-dimethylaminopropyl]carbodiimide hydrochloride and Sulfo-NHS (N-hydroxysuccinimide) (see Materials and Methods). In the second approach, we directly labeled the primary amines of the proteins, which are present also in the lysines, with the Alexa Fluor 488-TFP reactive dyes. And for the third approach, we carried out an indirect labeling method; here we initially conjugated our proteins at the primary amines with biotin molecules to make biotinylated-proteins. These biotinylated-proteins were then used for cell localization experiments, later the biotin molecules were detected using HRP-Streptavidin and the signal amplified using Tyramide signal amplification method.

After labeling the proteins using the first conjugation method, i.e. EDC-Sulfo-NHS Alexa fluor 488 labeling, we performed cell localization experiments in U-251 MG GBM cells. We observed that the IL-13-D2-NLS effectively localized to the nucleus at 1 hr., preceded by membrane and cytosolic localization at 15 min. We also performed Z-stack analysis to confirm the localization of the protein inside the nucleus. The Z-stack analysis demonstrated a nuclear localization of IL-13.E13K-D2-NLS (data not shown). On the other hand, IL-13-D2 did get internalized into the U-251 MG cells and was found to be in the cytosol, primarily in the peri-nuclear region, but it did not travel into the nucleus at either 15 min or 1 hr. of the experiment.

The above experiments strongly suggested an ability of IL-13-D2-NLS, but not IL-13-D2, to localize to U-251 GBM cells' nuclei. However, in order to obtain higher resolution pictures, we carried out a direct labeling of IL-13.E13K-D2-NLS and IL-13.E13K-D2 with the Alexa-fluor 488 dye. In this second approach, Alexa fluor 488 tetrafluorophenyl (TFP) reactive dye molecules attach directly to the primary amines of the amino acids of the proteins forming stable protein-dye conjugates. The protein-dye conjugates were visualized using either Coomassie-stained SDS-PAGE or fluorescence signals using Typhoon imaging system. The Typhoon scan showed protein-dye conjugates emitting fluorescence signals, while the unconjugated proteins did not produce any signals (not shown). We next repeated the localization experiments in U-251 MG cells and found what we had observed earlier. IL-13.E13K-D2-NLS localized to the nuclei at 1 hr. (not shown) whereas IL-13.E13K-D2 protein never trafficked into the nucleus.

In order to examine whether yet another visualization method would document the same nuclei-localization ability of our recombinant constructs; we decided to use a signal amplification method via tyramide molecules. We initially labeled our proteins using biotin-XX sulfosuccinimidyl ester (biotin-XX, SSE); which reacts very efficiently with the primary amines of the proteins forming stable protein-biotin conjugates. The biotinylated proteins were analyzed using SDS-PAGE/Western blot and the protein-biotin conjugates were detected using streptavidin-HRP. The Western blot indicated that both the proteins had been biotinylated. The number of biotins on each of these proteins was quantified by performing FluoReporter Biotin Quantitation assay based on standard curve. Using a quadratic fit equation, the IL-13.E13K-D2-NLS and IL-13.E13K-D2 had a similar degree of labeling (DOL) of 13.87 and 14.45 when labeled at a protein to dye molar ratio of 1:4 and 1:8, respectively. Next, these biotinylated proteins were tested in a neutralization of cytotoxicity assay (not shown). Both IL-13.E13K-D2-NLS and IL-13.E13K-D2 biotinylated proteins blocked the action of IL-13Rα2-specific cytotoxin-mediated U-251 MG cell killing indicating that these conjugates still compete for the receptor after undergoing biotinylation. The cell localization experiment was then conducted and the proteins were detected using Alexa fluor 488 and HRP-Streptavidin tyramide signal amplification procedure (see the Methods section). We found that in the case of IL-13.E13K-D2-NLS, at 5 min., the protein was bound to the cell membrane with some cytosolic localization. At 4 hr., cells had nuclear localization, whereas almost all the cells had a significant portion of the protein inside their nuclei at 8 hr. and 24 hr. For the IL-13.E13K-D2, at 5 min the protein was mostly found bound to the cell membrane with some molecules undergoing internalization. Whereas, at 8 and 24 hr. the protein was predominantly internalized and localized in the perinuclear region of cells. At 4 hr., the IL-13.E13K-D2 protein had cytosolic localization. Z-stack analyses of a 24 hr. experiment (not shown) establishes that the IL-13.E13K-D2 protein does not migrate to the nucleus.

We have also carried out experiments wherein we have labeled these proteins with different molar ratios of the biotin-dye. The protein:dye ratios used were 12, 8 and 4. When both IL13.E13K-D2-NLS and IL-13.E13K-D2 proteins were labeled at dye molar ratio of 12, we observed similar localization for these proteins as described, except we did not observe any nuclear localization at 4 hours. When we went down on the amount of dye (protein:dye molar ratio of 8 and 4 respectively) we observed more cells having nuclear localization at 4 hr. (Data not shown).

We also carried out cell localization experiment with another control protein, IL-13.E13K-NLS, which is devoid of Domain 2 of PE and should not be able to undergo endosomal translocation and subsequent nuclear transport; it should behave like the IL-13.E13K ligand alone. 12% SDS PAGE/ Western blot of the IL-13.E1K-D2-NLS, IL-13.E13K-D2, IL-13.E13K-NLS and the IL-13.E13K proteins conjugated with biotin and probed with streptavidin-HRP indicate that all the proteins are similarly labeled with biotin and also all the biotin-conjugated proteins bind to the IL-13Rα2 on GBM cells. The studies with IL-13.E13K-NLS and IL-13.E13K indicated our hypothesis to be correct, since this control protein did demonstrate perinuclear localization, but no nuclear transport at 24 hr. The same was observed in the cell localization studies using just the IL-13.E13K ligand. The IL-13.E13K accumulated mainly in the peri-nuclear region. Very few cells had these proteins in the nucleus. We have also carried out the localization studies for the IL-13.E13K-NLS and IL-13.E13K at 8, 4 hr and 5 min and they all demonstrate the results observed at 24 hr. (Data not shown).

IL-13.E13K-D2-NLS Localizes to the Nucleus of G48a GBM Cells.

We repeated the above experiments in another GBM cell line, G48a (13), which over-expresses IL-13Rα2. We obtained similar results as with the U-251 MG cells. Again, almost all the cells had the IL-13.E13K-D2-NLS protein inside their nuclei not only at 8 hr. and 24 hr., but already at 4 hr. of the experiment. Again, at 5 min, we observed mainly plasma membrane binding with some internalization of the protein. Z-stack analysis for the 24 hr. experiment establishes nuclear localization of the IL-13.E13K-D2-NLS protein. Similar results were observed for the IL-13.E13K-D2, IL-13.E13K-NLS and IL-13.E13K proteins in G48 cells as in U-251 MG cells; IL-13.E13K-D2, as well as IL-13.E13K-NLS and IL-13.E13K were not found to have any nuclear localization at any of the time-points and mainly had cytosolic/perinuclear localization with the time of experiment at 4, 8 and 24 hr. and cell membrane binding at 5 min.

IL-13.E13K-D2 NLS does not Localizes to the Nucleus of LN229 Cells.

We carried out identical experiments with biotin-labeled IL-13.E13K-D2-NLS in LN229 cells, very low expressors of IL-13Rα2. We observed that the protein displayed some binding to the cell surface with moderate internalization, but we did not observe any nuclear localization for the IL-13.E13K-D2-NLS protein at any of the experimental time points and no cytosolic or perinuclear localization for the IL-13.E13K-D2, IL-13.E13K-NLS and IL-13.E13K at 24 hr. contrary to what we observed in IL-13Rα2 high expressors, U-251 MG and G48a cells. Z-stack analysis for the IL-13.E13K-D2-NLS protein localization in an LN229 cell at 24 hr. depicts low internalization and no nuclear localization for the protein in these cells.

REFERENCES

1. Debinski W, Siegall C B, FitzGerald D, Pastan I. Substitution of foreign protein sequences into a chimeric toxin composed of transforming growth factor alpha and *Pseudomonas* exotoxin. Mol. Cell Biol. 1991 March; 11(3):1751-3.
2. Debinski W, Pastan I. Monovalent immunotoxin containing truncated form of *Pseudomonas* exotoxin as potent antitumor agent. Cancer Res. 1992 Oct. 1; 52(19):5379-85.
3. Debinski W, Obiri N I, Pastan I, Puri R K. A novel chimeric protein composed of interleukin 13 and *Pseudomonas* exotoxin is highly cytotoxic to human carcinoma cells expressing receptors for interleukin 13 and interleukin 4. J. Biol. Chem. 1995 Jul. 14; 270(28):16775-80.
4. Chiron M F, Fryling C M, FitzGerald D. Furin-mediated cleavage of *Pseudomonas* exotoxin-derived chimeric toxins. J. Biol. Chem. 1997 Dec. 12; 272(50):31707-11.
5. Inocencio N M, Moehring J M, Moehring T J. Furin activates *Pseudomonas* exotoxin A by specific cleavage in vivo and in vitro. J. Biol. Chem. 1994 Dec. 16; 269(50):31831-5.
6. Moehring J M, Inocencio N M, Robertson B J, Moehring T J. Expression of mouse furin in a Chinese hamster cell resistant to *Pseudomonas* exotoxin A and viruses complements the genetic lesion. J. Biol. Chem. 1993 Feb. 5; 268(4):2590-4.
7. Ogata M, Chaudhary V K, Pastan I, FitzGerald D J. Processing of *Pseudomonas* exotoxin by a cellular protease results in the generation of a 37,000-Da toxin fragment that is translocated to the cytosol. J. Biol. Chem. 1990 Nov. 25; 265(33):20678-85.
8. Jinno Y, Ogata M, Chaudhary V K, Willingham M C, Adhya S, FitzGerald D, Pastan I. Domain II mutants of *Pseudomonas* exotoxin deficient in translocation. J. Biol. Chem. 1989 Sep. 25; 264(27):15953-9.
9. Siegall C B, Ogata M, Pastan I, FitzGerald D J. Analysis of sequences in domain II of *Pseudomonas* exotoxin A which mediate translocation. Biochemistry 1991 Jul. 23; 30(29): 7154-9.
10. London S D, Schmaljohn A L, Dalrymple J M, Rice C M. Infectious enveloped RNA virus antigenic chimeras. Proc. Natl. Acad. Sci. U.S.A 1992 Jan. 1; 89(1):207-11.
11. Stenmark H, Moskaug J O, Madshus I H, Sandvig K, Olsnes S. Peptides fused to the amino-terminal end of diphtheria toxin are translocated to the cytosol. J. Cell Biol. 1991 June; 113(5):1025-32.
12. Stupp R, Dietrich P Y, Ostermann K S, Pica A, Maillard I, Maeder P, Meuli R, Janzer R, Pizzolato G, Miralbell R, et al. Promising survival for patients with newly diagnosed glioblastoma multiforme treated with concomitant radiation plus temozolomide followed by adjuvant temozolomide. J. Clin. Oncol. 2002 Mar. 1; 20(5):1375-82.
13. Debinski W, Gibo D M. Fos-related antigen 1 modulates malignant features of glioma cells. Mol. Cancer Res. 2005 April; 3(4):237-49.
14. Mintz A, Gibo D M, Slagle-Webb B, Christensen N D, Debinski W. IL-13Ralpha2 is a glioma-restricted receptor for interleukin-13. Neoplasia. 2002 September; 4(5):388-99.
15. Mintz A, Gibo D M, Madhankumar A B, Cladel N M, Christensen N D, Debinski W. Protein- and DNA-based active immunotherapy targeting interleukin-13 receptor alpha2. Cancer Biother. Radiopharm. 2008 October; 23(5): 581-9.
16. Wykosky J, Gibo D M, Stanton C, Debinski W. EphA2 as a novel molecular marker and target in glioblastoma multiforme. Mol. Cancer Res. 2005 October; 3(10):541-51.
17, Wykosky J, Gibo D M, Stanton C, Debinski W. Interleukin-13 receptor alpha 2, EphA2, and Fos-related antigen 1 as molecular denominators of high-grade astrocytomas and specific targets for combinatorial therapy. Clin. Cancer Res. 2008 Jan. 1; 14(1):199-208.
18. Debinski W. Drug cocktails for effective treatment of glioblastoma multiforme. Expert. Rev. Neurother. 2008 April; 8(4):515-7.
19, Debinski W, Gibo D M, Hulet S W, Connor J R, Gillespie G Y. Receptor for interleukin 13 is a marker and therapeutic target for human high-grade gliomas. Clin. Cancer Res. 1999 May; 5(5):985-90.
20. Saikali S, Avril T, Collet B, Hamlat A, Bansard J Y, Drenou B, Guegan Y, Quillien V. Expression of nine tumour antigens in a series of human glioblastoma multiforme: interest of EGFRvIII, IL-13Ralpha2, gp100 and TRP-2 for immunotherapy. J. Neurooncol. 2007 January; 81(2):139-48.
21. Debinski W, Gibo D M. Molecular expression analysis of restrictive receptor for interleukin 13, a brain tumor-associated cancer/testis antigen. Mol. Med. 2000 May; 6(5): 440-9.
22, Bernard J, Treton D, Vermot-Desroches C, Boden C, Horellou P, Angevin E, Galanaud P, Wijdenes J, Richard Y. Expression of interleukin 13 receptor in glioma and renal cell carcinoma: IL13Ralpha2 as a decoy receptor for IL13 1. Lab Invest 2001 September; 81(9):1223-31.
23. Kawakami K, Taguchi J, Murata T, Puri R K. The interleukin-13 receptor alpha2 chain: an essential component for binding and internalization but not for interleukin-13-induced signal transduction through the STATE pathway. Blood 2001 May 1; 97(9):2673-9.
24. Debinski W, Obiri N I, Powers S K, Pastan I, Puri R K. Human glioma cells overexpress receptors for interleukin 13 and are extremely sensitive to a novel chimeric protein composed of interleukin 13 and pseudomonas exotoxin. Clin. Cancer Res. 1995 November; 1(11):1253-8.
25. Madhankumar A B, Mintz A, Debinski W. Interleukin 13 mutants of enhanced avidity toward the glioma-associated receptor, IL13Ralpha2. Neoplasia. 2004 January; 6(1):15-22.
26. Thompson J P, Debinski W. Mutants of interleukin 13 with altered reactivity toward interleukin 13 receptors. J. Biol. Chem. 1999 Oct. 15; 274(42):29944-50.
27. Debinski W, Gibo D M, Obiri N I, Kealiher A, Puri R K. Novel anti-brain tumor cytotoxins specific for cancer cells. Nat. Biotechnol. 1998 May; 16(5):449-53.
28. Kalderon D, Roberts B L, Richardson W D, Smith A E. A short amino acid sequence able to specify nuclear location. Cell 1984 December; 39(3 Pt 2):499-509.
29. Hubner S, Xiao C Y, Jans D A. The protein kinase CK2 site (Ser111/112) enhances recognition of the simian virus 40 large T-antigen nuclear localization sequence by importin. J. Biol. Chem. 1997 Jul. 4; 272(27):17191-5.

30. Rihs H P, Peters R. Nuclear transport kinetics depend on phosphorylation-site-containing sequences flanking the karyophilic signal of the Simian virus 40 T-antigen. EMBO J. 1989 May; 8(5):1479-84.
31. Rihs H P, Jans D A, Fan H, Peters R. The rate of nuclear cytoplasmic protein transport is determined by the casein kinase II site flanking the nuclear localization sequence of the SV40 T-antigen. EMBO J. 1991 March; 10(3):633-9.
32. Xiao C Y, Hubner S, Jans D A. SV40 large tumor antigen nuclear import is regulated by the double-stranded DNA-dependent protein kinase site (serine 120) flanking the nuclear localization sequence. J. Biol. Chem. 1997 Aug. 29; 272(35):22191-8.
33. Madhankumar A B, Mintz A, Debinski W. Alanine-scanning mutagenesis of alpha-helix D segment of interleukin-13 reveals new functionally important residues of the cytokine. J. Biol. Chem. 2002 Nov. 8; 277(45):43194-205.
34. Mintz A, Gibo D M, Madhankumar A B, Debinski W. Molecular targeting with recombinant cytotoxins of interleukin-13 receptor alpha2-expressing glioma. J. Neurooncol. 2003 August; 64(1-2):117-23.
35. Jans D A, Xiao C Y, Lam M H. Nuclear targeting signal recognition: a key control point in nuclear transport? Bioessays 2000 June; 22(6):532-44.
36. Costantini D L, Chan C, Cai Z, Vallis K A, Reilly R M. (111) In-labeled trastuzumab (Herceptin) modified with nuclear localization sequences (NLS): an Auger electron-emitting radiotherapeutic agent for HER2/neu-amplified breast cancer. J. Nucl. Med. 2007 August; 48(8):1357-68.
37. Buchegger F, Perillo-Adamer F, Dupertuis Y M, Delaloye A B. Auger radiation targeted into DNA: a therapy perspective. Eur. J. Nucl. Med. Mol. Imaging 2006 November; 33(11):1352-63.
38. Goddu S M, Rao D V, Howell R W. Multicellular dosimetry for micrometastases: dependence of self-dose versus cross-dose to cell nuclei on type and energy of radiation and subcellular distribution of radionuclides. J. Nucl. Med. 1994 March; 35 (3):521-30.
39. Faraggi M, Gardin I, de Labriolle-Vaylet C, Moretti J L, Bok B D. The influence of tracer localization on the electron dose rate delivered to the cell nucleus. J. Nucl. Med. 1994 January; 35(1):113-9.
40. Madhankumar A B, Slagle-Webb B, Wang X, Yang Q X, Antonetti D A, Miller P A, Sheehan J M, Connor J R. Efficacy of interleukin-13 receptor-targeted liposomal doxorubicin in the intracranial brain tumor model. Mol. Cancer Ther. 2009 March; 8(3):648-54.
41. Liang H, Shin D S, Lee Y E, Nguyen D C, Trang T C, Pan A H, Huang S L, Chong D H, Berns M W. Subcellular phototoxicity of 5-aminolaevulinic acid (ALA). Lasers Surg. Med. 1998; 22(0:14-24.
42. Takemura T, Ohta N, Nakajima S, Sakata I. Critical importance of the triplet lifetime of photosensitizer in photodynamic therapy of tumor. Photochem. Photobiol. 1989 September; 50(3):339-44.

The foregoing is illustrative of the present invention, and is not to be construed as limiting thereof. The invention is defined by the following claims, with equivalents of the claims to be included therein.

---

That which is claimed is:

1. A compound comprising, in combination:
    an IL-13Rα2 binding ligand, wherein said IL-13Rα2 binding ligand is IL-13, a mutant of IL-13, or an IL-13Rα2 binding fragment thereof;
    at least one effector molecule;
    a cytosol localization element covalently coupled between said binding ligand and said at least one effector molecule; and
    a subcellular compartment localization signal element covalently coupled between said binding ligand and said at least one effector molecule,
    wherein said compound is a fusion protein or a covalent conjugate.

2. The compound of claim 1, wherein each of the IL-13Rα2 binding ligand, the cytosol localization element, and the subcellular compartment localization signal element is a protein or peptide.

3. The compound of claim 1, wherein said cytosol localization element is a *Pseudomonas* exotoxin or diphtheria toxin translocation domain.

4. The compound of claim 3, wherein said cytosol localization element is a *Pseudomonas* exotoxin A D2 segment.

5. The compound of claim 1, wherein said subcellular compartment localization signal element is a nuclear localization element or a lysosomal localization element.

6. The compound of claim 5, wherein said subcellular compartment localization signal element is an SV40 T antigen nuclear localization signal.

7. The compound of claim 1, wherein said at least one effector molecule consists of two effector molecules.

8. The compound of claim 1, wherein said at least one effector molecule comprises a toxin or an amphipathic antimicrobial peptide.

9. The compound of claim 8, wherein said at least one effector molecule comprises a toxin selected from the group consisting of diphtheria toxin and *Pseudomonas* exotoxin.

10. The compound of claim 8, wherein said at least one effector molecule comprises an amphipathic antimicrobial peptide comprising a sequence selected from the group consisting of: (KLAKLAK)$_2$ (SEQ ID NO: 60); (KLAKKLA)$_2$ (SEQ ID NO: 61); (KAAKKAA)$_2$ (SEQ ID NO: 62) and (KLGKKLG)$_2$ (SEQ ID NO: 63).

11. The compound of claim 1, wherein said at least one effector molecule comprises a therapeutic agent, a detectable group, a lipid, or a liposome.

12. The compound of claim 1, wherein said at least one effector molecule comprises a chemotherapeutic agent.

13. The compound of claim 12, wherein the chemotherapeutic agent is selected from the group consisting of: methotrexate, daunomycin, mitomycin C, cisplatin, vincristine, epirubicin, fluorouracil, verapamil, cyclophosphamide, cytosine arabinoside, aminopterin, bleomycin, mitomycin C, democolcine, etoposide, mithramycin, chlorambucil, melphalan, daunorubicin, doxorubicin, tamosifen, paclitaxel, vincristin, vinblastine, camptothecin, actinomycin D, and cytarabine.

14. The compound of claim 12, wherein the chemotherapeutic agent is doxorubicin or daunorubicon.

15. The compound of claim 1, wherein said IL-13Rα2 binding ligand is an IL-13 mutant.

16. The compound of claim 15, wherein said IL-13 mutant is IL-13.E13K.

17. A composition comprising the compound of claim 1 and a pharmaceutical carrier.

18. The composition of claim 17, wherein said composition is sterile.

19. The compound of claim 1, wherein said compound has the formula: A-B-C-D-E, wherein:
    A is said IL-13Rα2 binding ligand;
    B is said cytosol localization element;
    C is said subcellular compartment localization signal element;
    D is an effector molecule; and
    E is present or absent and when present is a second effector molecule.

20. The compound of claim 1, wherein said compound has the formula: A-C-B-D-E, wherein:
    A is said IL-13Rα2 binding ligand;
    B is said cytosol localization element;
    C is said subcellular compartment localization signal element;
    D is an effector molecule; and
    E is present or absent and when present is a second effector molecule.

* * * * *

SEQUENCE LISTING

```
<160> NUMBER OF SEQ ID NOS: 66

<210> SEQ ID NO 1
<211> LENGTH: 9
<212> TYPE: PRT
<213> ORGANISM: Artificial
<220> FEATURE:
<223> OTHER INFORMATION: Targeting peptide sequence

<400> SEQUENCE: 1

Cys Gly Glu Met Gly Trp Val Arg Cys
1               5

<210> SEQ ID NO 2
<211> LENGTH: 14
<212> TYPE: PRT
<213> ORGANISM: Artificial
<220> FEATURE:
<223> OTHER INFORMATION: Targeting peptide sequence

<400> SEQUENCE: 2

Ala Cys Gly Glu Met Gly Trp Val Arg Cys Gly Gly Gly Ser
1               5                   10

<210> SEQ ID NO 3
<211> LENGTH: 9
<212> TYPE: PRT
<213> ORGANISM: Artificial
<220> FEATURE:
<223> OTHER INFORMATION: Targeting peptide sequence

<400> SEQUENCE: 3

Cys Leu Pro Gln Leu Trp Leu Phe Cys
1               5
```

```
<210> SEQ ID NO 4
<211> LENGTH: 14
<212> TYPE: PRT
<213> ORGANISM: Artificial
<220> FEATURE:
<223> OTHER INFORMATION: Targeting peptide sequence

<400> SEQUENCE: 4

Ala Cys Leu Pro Gln Leu Trp Leu Phe Cys Gly Gly Gly Ser
1               5                   10

<210> SEQ ID NO 5
<211> LENGTH: 9
<212> TYPE: PRT
<213> ORGANISM: Artificial
<220> FEATURE:
<223> OTHER INFORMATION: Targeting peptide sequence

<400> SEQUENCE: 5

Cys Ser Pro Phe Leu His Leu Leu Cys
1               5

<210> SEQ ID NO 6
<211> LENGTH: 14
<212> TYPE: PRT
<213> ORGANISM: Artificial
<220> FEATURE:
<223> OTHER INFORMATION: Targeting peptide sequence

<400> SEQUENCE: 6

Ala Cys Ser Pro Phe Leu His Leu Leu Cys Gly Gly Gly Ser
1               5                   10

<210> SEQ ID NO 7
<211> LENGTH: 8
<212> TYPE: PRT
<213> ORGANISM: Artificial
<220> FEATURE:
<223> OTHER INFORMATION: Targeting peptide sequence

<400> SEQUENCE: 7

Ser Glu Met Gly Trp Val Arg Cys
1               5

<210> SEQ ID NO 8
<211> LENGTH: 7
<212> TYPE: PRT
<213> ORGANISM: Artificial
<220> FEATURE:
<223> OTHER INFORMATION: Targeting peptide sequence

<400> SEQUENCE: 8

Gly Asp Met Gly Trp Val Arg
1               5

<210> SEQ ID NO 9
<211> LENGTH: 7
<212> TYPE: PRT
<213> ORGANISM: Artificial
<220> FEATURE:
<223> OTHER INFORMATION: Targeting peptide sequence

<400> SEQUENCE: 9

Ser Asp Trp Gly Trp Val Arg
1               5
```

```
<210> SEQ ID NO 10
<211> LENGTH: 7
<212> TYPE: PRT
<213> ORGANISM: Artificial
<220> FEATURE:
<223> OTHER INFORMATION: Targeting peptide sequence

<400> SEQUENCE: 10

Gly Asp Tyr Gly Trp Val Arg
1               5

<210> SEQ ID NO 11
<211> LENGTH: 7
<212> TYPE: PRT
<213> ORGANISM: Artificial
<220> FEATURE:
<223> OTHER INFORMATION: Targeting peptide sequence

<400> SEQUENCE: 11

Ser Glu Ile Gly Trp Val Arg
1               5

<210> SEQ ID NO 12
<211> LENGTH: 7
<212> TYPE: PRT
<213> ORGANISM: Artificial
<220> FEATURE:
<223> OTHER INFORMATION: Targeting peptide sequence

<400> SEQUENCE: 12

Gly Glu Ile Ser Trp Val Arg
1               5

<210> SEQ ID NO 13
<211> LENGTH: 7
<212> TYPE: PRT
<213> ORGANISM: Artificial
<220> FEATURE:
<223> OTHER INFORMATION: Targeting peptide sequence

<400> SEQUENCE: 13

Gly Glu Met Ala Trp Val Arg
1               5

<210> SEQ ID NO 14
<211> LENGTH: 7
<212> TYPE: PRT
<213> ORGANISM: Artificial
<220> FEATURE:
<223> OTHER INFORMATION: Targeting peptide sequence

<400> SEQUENCE: 14

Gly Glu Met Gly Phe Val Arg
1               5

<210> SEQ ID NO 15
<211> LENGTH: 7
<212> TYPE: PRT
<213> ORGANISM: Artificial
<220> FEATURE:
<223> OTHER INFORMATION: Targeting peptide sequence

<400> SEQUENCE: 15

Gly Glu Met Gly His Val Arg
1               5

<210> SEQ ID NO 16
```

```
<211> LENGTH: 7
<212> TYPE: PRT
<213> ORGANISM: Artificial
<220> FEATURE:
<223> OTHER INFORMATION: Targeting peptide sequence

<400> SEQUENCE: 16

Gly Glu Met Ser Tyr Val Arg
1               5

<210> SEQ ID NO 17
<211> LENGTH: 7
<212> TYPE: PRT
<213> ORGANISM: Artificial
<220> FEATURE:
<223> OTHER INFORMATION: Targeting peptide sequence

<400> SEQUENCE: 17

Gly Glu Met Gly Trp Pro Arg
1               5

<210> SEQ ID NO 18
<211> LENGTH: 7
<212> TYPE: PRT
<213> ORGANISM: Artificial
<220> FEATURE:
<223> OTHER INFORMATION: Targeting peptide sequence

<400> SEQUENCE: 18

Gly Glu Met Gly Trp Thr Arg
1               5

<210> SEQ ID NO 19
<211> LENGTH: 7
<212> TYPE: PRT
<213> ORGANISM: Artificial
<220> FEATURE:
<223> OTHER INFORMATION: Targeting peptide sequence

<400> SEQUENCE: 19

Gly Glu Met Gly Trp Asn Lys
1               5

<210> SEQ ID NO 20
<211> LENGTH: 7
<212> TYPE: PRT
<213> ORGANISM: Artificial
<220> FEATURE:
<223> OTHER INFORMATION: Targeting peptide sequence

<400> SEQUENCE: 20

Gly Glu Met Gly Trp Asn His
1               5

<210> SEQ ID NO 21
<211> LENGTH: 7
<212> TYPE: PRT
<213> ORGANISM: Artificial
<220> FEATURE:
<223> OTHER INFORMATION: Targeting peptide sequence

<400> SEQUENCE: 21

Ala Pro Gln Leu Trp Leu Phe
1               5

<210> SEQ ID NO 22
<211> LENGTH: 7
```

```
<212> TYPE: PRT
<213> ORGANISM: Artificial
<220> FEATURE:
<223> OTHER INFORMATION: Targeting peptide sequence

<400> SEQUENCE: 22

Ile Pro Gln Leu Trp Leu Phe
1               5

<210> SEQ ID NO 23
<211> LENGTH: 7
<212> TYPE: PRT
<213> ORGANISM: Artificial
<220> FEATURE:
<223> OTHER INFORMATION: Targeting peptide sequence

<400> SEQUENCE: 23

Val Pro Gln Leu Trp Leu Phe
1               5

<210> SEQ ID NO 24
<211> LENGTH: 7
<212> TYPE: PRT
<213> ORGANISM: Artificial
<220> FEATURE:
<223> OTHER INFORMATION: Targeting peptide sequence

<400> SEQUENCE: 24

Met Pro Gln Leu Trp Leu Phe
1               5

<210> SEQ ID NO 25
<211> LENGTH: 7
<212> TYPE: PRT
<213> ORGANISM: Artificial
<220> FEATURE:
<223> OTHER INFORMATION: Targeting peptide sequence

<400> SEQUENCE: 25

Leu Val Gln Leu Trp Leu Phe
1               5

<210> SEQ ID NO 26
<211> LENGTH: 7
<212> TYPE: PRT
<213> ORGANISM: Artificial
<220> FEATURE:
<223> OTHER INFORMATION: Targeting peptide sequence

<400> SEQUENCE: 26

Leu Thr Gln Leu Trp Leu Phe
1               5

<210> SEQ ID NO 27
<211> LENGTH: 7
<212> TYPE: PRT
<213> ORGANISM: Artificial
<220> FEATURE:
<223> OTHER INFORMATION: Targeting peptide sequence

<400> SEQUENCE: 27

Leu Asn Gln Leu Trp Leu Phe
1               5

<210> SEQ ID NO 28
<211> LENGTH: 7
<212> TYPE: PRT
```

<213> ORGANISM: Artificial
<220> FEATURE:
<223> OTHER INFORMATION: Targeting peptide sequence

<400> SEQUENCE: 28

Leu Pro Asn Leu Trp Leu Phe
1               5

<210> SEQ ID NO 29
<211> LENGTH: 7
<212> TYPE: PRT
<213> ORGANISM: Artificial
<220> FEATURE:
<223> OTHER INFORMATION: Targeting peptide sequence

<400> SEQUENCE: 29

Leu Pro Asp Leu Trp Leu Phe
1               5

<210> SEQ ID NO 30
<211> LENGTH: 7
<212> TYPE: PRT
<213> ORGANISM: Artificial
<220> FEATURE:
<223> OTHER INFORMATION: Targeting peptide sequence

<400> SEQUENCE: 30

Leu Pro Glu Leu Trp Leu Phe
1               5

<210> SEQ ID NO 31
<211> LENGTH: 7
<212> TYPE: PRT
<213> ORGANISM: Artificial
<220> FEATURE:
<223> OTHER INFORMATION: Targeting peptide sequence

<400> SEQUENCE: 31

Leu Pro His Leu Trp Leu Phe
1               5

<210> SEQ ID NO 32
<211> LENGTH: 7
<212> TYPE: PRT
<213> ORGANISM: Artificial
<220> FEATURE:
<223> OTHER INFORMATION: Targeting peptide sequence

<400> SEQUENCE: 32

Leu Pro Gln Ala Phe Ala Trp
1               5

<210> SEQ ID NO 33
<211> LENGTH: 7
<212> TYPE: PRT
<213> ORGANISM: Artificial
<220> FEATURE:
<223> OTHER INFORMATION: Targeting peptide sequence

<400> SEQUENCE: 33

Leu Pro Gln Ile Phe Ile His
1               5

<210> SEQ ID NO 34
<211> LENGTH: 7
<212> TYPE: PRT
<213> ORGANISM: Artificial

```
<220> FEATURE:
<223> OTHER INFORMATION: Targeting peptide sequence

<400> SEQUENCE: 34

Leu Pro Gln Val His Val Tyr
1               5

<210> SEQ ID NO 35
<211> LENGTH: 7
<212> TYPE: PRT
<213> ORGANISM: Artificial
<220> FEATURE:
<223> OTHER INFORMATION: Targeting peptide sequence

<400> SEQUENCE: 35

Leu Pro Gln Met Tyr Met Tyr
1               5

<210> SEQ ID NO 36
<211> LENGTH: 7
<212> TYPE: PRT
<213> ORGANISM: Artificial
<220> FEATURE:
<223> OTHER INFORMATION: Targeting peptide sequence

<400> SEQUENCE: 36

Met Asn His Met Tyr Met Tyr
1               5

<210> SEQ ID NO 37
<211> LENGTH: 7
<212> TYPE: PRT
<213> ORGANISM: Artificial
<220> FEATURE:
<223> OTHER INFORMATION: Targeting peptide sequence

<400> SEQUENCE: 37

Val Thr Glu Val His Val His
1               5

<210> SEQ ID NO 38
<211> LENGTH: 7
<212> TYPE: PRT
<213> ORGANISM: Artificial
<220> FEATURE:
<223> OTHER INFORMATION: Targeting peptide sequence

<400> SEQUENCE: 38

Gly Pro Phe Leu His Leu Leu
1               5

<210> SEQ ID NO 39
<211> LENGTH: 7
<212> TYPE: PRT
<213> ORGANISM: Artificial
<220> FEATURE:
<223> OTHER INFORMATION: Targeting peptide sequence

<400> SEQUENCE: 39

Ser Val Phe Leu His Leu Leu
1               5

<210> SEQ ID NO 40
<211> LENGTH: 7
<212> TYPE: PRT
<213> ORGANISM: Artificial
<220> FEATURE:
```

```
<223> OTHER INFORMATION: Targeting peptide sequence

<400> SEQUENCE: 40

Ser Thr Phe Leu His Leu Leu
1               5

<210> SEQ ID NO 41
<211> LENGTH: 7
<212> TYPE: PRT
<213> ORGANISM: Artificial
<220> FEATURE:
<223> OTHER INFORMATION: Targeting peptide sequence

<400> SEQUENCE: 41

Ser Asn Trp Leu His Leu Leu
1               5

<210> SEQ ID NO 42
<211> LENGTH: 7
<212> TYPE: PRT
<213> ORGANISM: Artificial
<220> FEATURE:
<223> OTHER INFORMATION: Targeting peptide sequence

<400> SEQUENCE: 42

Ser Pro His Leu His Leu Leu
1               5

<210> SEQ ID NO 43
<211> LENGTH: 7
<212> TYPE: PRT
<213> ORGANISM: Artificial
<220> FEATURE:
<223> OTHER INFORMATION: Targeting peptide sequence

<400> SEQUENCE: 43

Ser Pro Tyr Leu His Leu Leu
1               5

<210> SEQ ID NO 44
<211> LENGTH: 7
<212> TYPE: PRT
<213> ORGANISM: Artificial
<220> FEATURE:
<223> OTHER INFORMATION: Targeting peptide sequence

<400> SEQUENCE: 44

Ser Pro Phe Ala His Leu Leu
1               5

<210> SEQ ID NO 45
<211> LENGTH: 7
<212> TYPE: PRT
<213> ORGANISM: Artificial
<220> FEATURE:
<223> OTHER INFORMATION: Targeting peptide sequence

<400> SEQUENCE: 45

Ser Pro Phe Ile His Leu Leu
1               5

<210> SEQ ID NO 46
<211> LENGTH: 7
<212> TYPE: PRT
<213> ORGANISM: Artificial
<220> FEATURE:
<223> OTHER INFORMATION: Targeting peptide sequence
```

```
<400> SEQUENCE: 46

Ser Pro Phe Val His Leu Leu
1               5

<210> SEQ ID NO 47
<211> LENGTH: 7
<212> TYPE: PRT
<213> ORGANISM: Artificial
<220> FEATURE:
<223> OTHER INFORMATION: Targeting peptide sequence

<400> SEQUENCE: 47

Ser Pro Phe Met His Leu Leu
1               5

<210> SEQ ID NO 48
<211> LENGTH: 7
<212> TYPE: PRT
<213> ORGANISM: Artificial
<220> FEATURE:
<223> OTHER INFORMATION: Targeting peptide sequence

<400> SEQUENCE: 48

Ser Pro Phe Leu Trp Leu Leu
1               5

<210> SEQ ID NO 49
<211> LENGTH: 7
<212> TYPE: PRT
<213> ORGANISM: Artificial
<220> FEATURE:
<223> OTHER INFORMATION: Targeting peptide sequence

<400> SEQUENCE: 49

Ser Pro Phe Leu Phe Ala Ala
1               5

<210> SEQ ID NO 50
<211> LENGTH: 7
<212> TYPE: PRT
<213> ORGANISM: Artificial
<220> FEATURE:
<223> OTHER INFORMATION: Targeting peptide sequence

<400> SEQUENCE: 50

Ser Pro Phe Leu Phe Ile Ile
1               5

<210> SEQ ID NO 51
<211> LENGTH: 7
<212> TYPE: PRT
<213> ORGANISM: Artificial
<220> FEATURE:
<223> OTHER INFORMATION: Targeting peptide sequence

<400> SEQUENCE: 51

Ser Pro Phe Leu His Val Val
1               5

<210> SEQ ID NO 52
<211> LENGTH: 7
<212> TYPE: PRT
<213> ORGANISM: Artificial
<220> FEATURE:
<223> OTHER INFORMATION: Targeting peptide sequence
```

```
<400> SEQUENCE: 52

Ser Pro Phe Leu Tyr Met Met
1               5

<210> SEQ ID NO 53
<211> LENGTH: 7
<212> TYPE: PRT
<213> ORGANISM: Artificial
<220> FEATURE:
<223> OTHER INFORMATION: Targeting peptide sequence

<400> SEQUENCE: 53

Gly Asn Tyr Met Tyr Met Met
1               5

<210> SEQ ID NO 54
<211> LENGTH: 7
<212> TYPE: PRT
<213> ORGANISM: Artificial
<220> FEATURE:
<223> OTHER INFORMATION: Targeting peptide sequence

<400> SEQUENCE: 54

Gly Thr His Val Phe Val Ile
1               5

<210> SEQ ID NO 55
<211> LENGTH: 7
<212> TYPE: PRT
<213> ORGANISM: Simian virus 40

<400> SEQUENCE: 55

Pro Lys Lys Lys Arg Lys Val
1               5

<210> SEQ ID NO 56
<211> LENGTH: 16
<212> TYPE: PRT
<213> ORGANISM: Artificial
<220> FEATURE:
<223> OTHER INFORMATION: Xenopus nucleoplasmin NLS consensus sequence
<220> FEATURE:
<221> NAME/KEY: misc_feature
<222> LOCATION: (3)..(12)
<223> OTHER INFORMATION: Xaa can be any naturally occurring amino acid

<400> SEQUENCE: 56

Lys Arg Xaa Xaa Xaa Xaa Xaa Xaa Xaa Xaa Xaa Xaa Lys Lys Lys Leu
1               5                   10                  15

<210> SEQ ID NO 57
<211> LENGTH: 11
<212> TYPE: PRT
<213> ORGANISM: Homo sapiens

<400> SEQUENCE: 57

Arg Lys Arg Ser His Ala Gly Tyr Gln Thr Ile
1               5                   10

<210> SEQ ID NO 58
<211> LENGTH: 23
<212> TYPE: PRT
<213> ORGANISM: Homo sapiens

<400> SEQUENCE: 58

Arg Leu Lys Arg Met Gln Ala Gln Pro Pro Gly Tyr Arg His Val Ala
```

```
Asp Gly Glu Asp His Ala Val
            20

<210> SEQ ID NO 59
<211> LENGTH: 20
<212> TYPE: PRT
<213> ORGANISM: Homo sapiens

<400> SEQUENCE: 59

Arg Gly Gln Gly Ser Thr Asp Glu Gly Thr Ala Asp Glu Arg Ala Pro
1               5                   10                  15

Leu Ile Arg Thr
            20

<210> SEQ ID NO 60
<211> LENGTH: 14
<212> TYPE: PRT
<213> ORGANISM: Artificial
<220> FEATURE:
<223> OTHER INFORMATION: Amphipathic antimicrobial peptide sequence

<400> SEQUENCE: 60

Lys Leu Ala Lys Leu Ala Lys Lys Leu Ala Lys Leu Ala Lys
1               5                   10

<210> SEQ ID NO 61
<211> LENGTH: 14
<212> TYPE: PRT
<213> ORGANISM: Artificial
<220> FEATURE:
<223> OTHER INFORMATION: Amphipathic antimicrobial peptide sequence

<400> SEQUENCE: 61

Lys Leu Ala Lys Lys Leu Ala Lys Leu Ala Lys Lys Leu Ala
1               5                   10

<210> SEQ ID NO 62
<211> LENGTH: 14
<212> TYPE: PRT
<213> ORGANISM: Artificial
<220> FEATURE:
<223> OTHER INFORMATION: Amphipathic antimicrobial peptide sequence

<400> SEQUENCE: 62

Lys Ala Ala Lys Lys Ala Ala Lys Ala Ala Lys Lys Ala Ala
1               5                   10

<210> SEQ ID NO 63
<211> LENGTH: 14
<212> TYPE: PRT
<213> ORGANISM: Artificial
<220> FEATURE:
<223> OTHER INFORMATION: Amphipathic antimicrobial peptide sequence

<400> SEQUENCE: 63

Lys Leu Gly Lys Lys Leu Gly Lys Leu Gly Lys Lys Leu Gly
1               5                   10

<210> SEQ ID NO 64
<211> LENGTH: 7
<212> TYPE: PRT
<213> ORGANISM: Artificial
<220> FEATURE:
<223> OTHER INFORMATION: General formula for targeting peptide
<220> FEATURE:
```

```
<221> NAME/KEY: MISC_FEATURE
<222> LOCATION: (1)..(1)
<223> OTHER INFORMATION: Optionally present is a capping group, a
      linking group, an amino acid optionally terminated by a capping
      group or linking group, or a peptide consisting of from 2 to 6 or
      10 additional amino acids optionally terminated by a capping group
      or linking group
<220> FEATURE:
<221> NAME/KEY: MISC_FEATURE
<222> LOCATION: (1)..(1)
<223> OTHER INFORMATION: Xaa is G or S
<220> FEATURE:
<221> NAME/KEY: MISC_FEATURE
<222> LOCATION: (2)..(2)
<223> OTHER INFORMATION: Xaa is a negatively charged amino acid
<220> FEATURE:
<221> NAME/KEY: MISC_FEATURE
<222> LOCATION: (3)..(3)
<223> OTHER INFORMATION: Xaa is a large hydrophobic amino acid
<220> FEATURE:
<221> NAME/KEY: MISC_FEATURE
<222> LOCATION: (4)..(4)
<223> OTHER INFORMATION: Xaa is a small amino acid
<220> FEATURE:
<221> NAME/KEY: MISC_FEATURE
<222> LOCATION: (5)..(5)
<223> OTHER INFORMATION: Xaa is a large or aromatic amino acid
<220> FEATURE:
<221> NAME/KEY: MISC_FEATURE
<222> LOCATION: (6)..(6)
<223> OTHER INFORMATION: Xaa is preferably a hydrophobic or neutral
      amino acid
<220> FEATURE:
<221> NAME/KEY: MISC_FEATURE
<222> LOCATION: (7)..(7)
<223> OTHER INFORMATION: Xaa is a positively charged amino acid
<220> FEATURE:
<221> NAME/KEY: MISC_FEATURE
<222> LOCATION: (7)..(7)
<223> OTHER INFORMATION: Optionally present is a capping group, a
      linking group, an amino acid optionally terminated by a capping
      group or linking group, or a peptide consisting of from 2 to 6 or
      10 additional amino acids optionally terminated by a capping group
      or linking group

<400> SEQUENCE: 64

Xaa Xaa Xaa Xaa Xaa Xaa Xaa
1               5

<210> SEQ ID NO 65
<211> LENGTH: 7
<212> TYPE: PRT
<213> ORGANISM: Artificial
<220> FEATURE:
<223> OTHER INFORMATION: General formula for targeting peptide
<220> FEATURE:
<221> NAME/KEY: MISC_FEATURE
<222> LOCATION: (1)..(1)
<223> OTHER INFORMATION: Optionally present is a capping group, a
      linking group, an amino acid optionally terminated by a capping
      group or linking group, or a peptide consisting of from 2 to 6 or
      10 additional amino acids optionally terminated by a capping group
      or linking group
<220> FEATURE:
<221> NAME/KEY: MISC_FEATURE
<222> LOCATION: (1)..(1)
<223> OTHER INFORMATION: Xaa is a hydrophobic amino acid
<220> FEATURE:
<221> NAME/KEY: MISC_FEATURE
<222> LOCATION: (2)..(2)
<223> OTHER INFORMATION: Xaa is preferably a hydrophobic or neutral
      amino acid
<220> FEATURE:
<221> NAME/KEY: MISC_FEATURE
<222> LOCATION: (3)..(3)
<223> OTHER INFORMATION: Xaa is a charged or uncharged polar amino acid
<220> FEATURE:
```

```
<221> NAME/KEY: MISC_FEATURE
<222> LOCATION: (4)..(4)
<223> OTHER INFORMATION: Xaa is a hydrophobic amino acid
<220> FEATURE:
<221> NAME/KEY: MISC_FEATURE
<222> LOCATION: (5)..(5)
<223> OTHER INFORMATION: Xaa is a large or aromatic amino acid
<220> FEATURE:
<221> NAME/KEY: MISC_FEATURE
<222> LOCATION: (6)..(6)
<223> OTHER INFORMATION: Xaa is a hydrophobic amino acid
<220> FEATURE:
<221> NAME/KEY: MISC_FEATURE
<222> LOCATION: (7)..(7)
<223> OTHER INFORMATION: Xaa is a large or aromatic amino acid
<220> FEATURE:
<221> NAME/KEY: MISC_FEATURE
<222> LOCATION: (7)..(7)
<223> OTHER INFORMATION: Optionally present is a capping group, a
      linking group, an amino acid optionally terminated by a capping
      group or linking group, or a peptide consisting of from 2 to 6 or
      10 additional amino acids optionally terminated by a capping group
      or linking group

<400> SEQUENCE: 65

Xaa Xaa Xaa Xaa Xaa Xaa Xaa
1               5

<210> SEQ ID NO 66
<211> LENGTH: 7
<212> TYPE: PRT
<213> ORGANISM: Artificial
<220> FEATURE:
<223> OTHER INFORMATION: General formula for targeting peptide
<220> FEATURE:
<221> NAME/KEY: MISC_FEATURE
<222> LOCATION: (1)..(1)
<223> OTHER INFORMATION: Optionally present is a capping group, a
      linking group, an amino acid optionally terminated by a capping
      group or linking group, or a peptide consisting of from 2 to 6 or
      10 additional amino acids optionally terminated by a capping group
      or linking group
<220> FEATURE:
<221> NAME/KEY: MISC_FEATURE
<222> LOCATION: (1)..(1)
<223> OTHER INFORMATION: Xaa is S or G
<220> FEATURE:
<221> NAME/KEY: MISC_FEATURE
<222> LOCATION: (2)..(2)
<223> OTHER INFORMATION: Xaa is preferably a hydrophobic or neutral
      amino acid
<220> FEATURE:
<221> NAME/KEY: MISC_FEATURE
<222> LOCATION: (3)..(3)
<223> OTHER INFORMATION: Xaa is a large or aromatic amino acid
<220> FEATURE:
<221> NAME/KEY: MISC_FEATURE
<222> LOCATION: (4)..(4)
<223> OTHER INFORMATION: Xaa is a hydrophobic amino acid
<220> FEATURE:
<221> NAME/KEY: MISC_FEATURE
<222> LOCATION: (5)..(5)
<223> OTHER INFORMATION: Xaa is a large or aromatic amino acid
<220> FEATURE:
<221> NAME/KEY: MISC_FEATURE
<222> LOCATION: (6)..(6)
<223> OTHER INFORMATION: Xaa is a hydrophobic amino acid
<220> FEATURE:
<221> NAME/KEY: MISC_FEATURE
<222> LOCATION: (7)..(7)
<223> OTHER INFORMATION: Xaa is a hydrophobic amino acid
<220> FEATURE:
<221> NAME/KEY: MISC_FEATURE
<222> LOCATION: (7)..(7)
<223> OTHER INFORMATION: Optionally present is a capping group, a
      linking group, an amino acid optionally terminated by a capping
      group or linking group, or a peptide consisting of from 2 to 6 or
```

```
        10 additional amino acids optionally terminated by a capping group
        or linking group

<400> SEQUENCE: 66

Xaa Xaa Xaa Xaa Xaa Xaa Xaa
1               5
```